(12) United States Patent
Dixson et al.

(10) Patent No.: US 7,767,667 B2
(45) Date of Patent: Aug. 3, 2010

(54) PESTICIDAL HETEROCYCLES

(75) Inventors: John A. Dixson, Newtown, PA (US);
Zeinab M. Elshenawy, Plainsboro, NJ (US); Harvey R. Wendt, Medford Lakes, NJ (US); Saroj Sehgel, Princeton Junction, NJ (US); Robert H. Henrie, II, Pennington, NJ (US); David M. Roush, Princeton, NJ (US); Ping Ding, Lawrenceville, NJ (US); John W. Lyga, Basking Ridge, NJ (US); Stephen F. Donovan, Revere, PA (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 12/196,893

(22) Filed: Aug. 22, 2008

(65) Prior Publication Data

US 2009/0012070 A1 Jan. 8, 2009

Related U.S. Application Data

(62) Division of application No. 10/512,377, filed as application No. PCT/US03/13127 on Apr. 28, 2003, now Pat. No. 7,417,057.

(60) Provisional application No. 60/376,363, filed on Apr. 29, 2002.

(51) Int. Cl.
*A01N 43/50* (2006.01)
*A61P 7/04* (2006.01)
*C07D 233/20* (2006.01)
*C07D 405/04* (2006.01)
*C07D 403/04* (2006.01)

(52) U.S. Cl. ............... 514/229.2; 514/256; 514/365; 514/374; 514/397; 514/400; 514/401; 514/402; 514/414; 544/66; 544/333; 546/115; 548/146; 548/237; 548/311.7; 548/347.1; 548/529

(58) Field of Classification Search ............... None
See application file for complete search history.

(56) References Cited

U.S. PATENT DOCUMENTS

| | | | |
|---|---|---|---|
| 2,731,471 A | 1/1956 | Sahyun | |
| 2,948,724 A | 8/1960 | Sahyun | |
| 4,415,741 A | 11/1983 | Kabbe et al. | |
| 4,634,705 A | 1/1987 | DeBernardis et al. | |
| 5,658,938 A | 8/1997 | Geerts et al. | |
| 6,313,311 B1 | 11/2001 | Karjalainen et al. | |

FOREIGN PATENT DOCUMENTS

| | | |
|---|---|---|
| GB | 2 256 135 | 12/1992 |
| NE | 6705095 | 10/1967 |
| WO | WO97/12874 | 4/1997 |
| WO | WO01/51472 | 7/2001 |

OTHER PUBLICATIONS

Patent Abstracts of Japan, vol. 012, No. 462 (C-549), Dec. 5, 1988 and JP63-183579A (SS Pharmaceut Co Ltd), Jul. 28, 1988, 3,6,8-trichloro-4- (4,5-dichloro-2-pyrryl)-2H-1-bensopyran.
Zhang et al., "Medetomidine analogs as alpha-2 adrenergic ligands," Journal of Medicinal Chemistry, American Chemical Society, Washington, US, vol. 40, 1997, pp. 3014-3024, XP002108693.
P. Grandclaudon, A. Lablanche-Combier: Tetrahedron, vol. 29, 1973, pp. 651-658, XP002334165.
A.C. Jambut-Absil et al., "Charge transfer complexes of drugs with iodine investigation by UV/visible spectroscopy," International Journal of Pharmaceutics, vol. 35, 1987, pp. 129-137, XP002334166.
John F. Debernardis, "Conformationally Defined Adrenergic Agents," Journal of Medicinal Chemistry, pp. 463-467, 1986.
D. L. Camper, et al., "Restricted Analog Design Strategies of Arylalkylimidazole Insecticides," Discovery Research, Dow AgroSciences (Indianapolis, IN).

*Primary Examiner*—Kamal A Saeed

(57) ABSTRACT

It has now been found that certain novel heterocyclic derivitives have provided unexpected insecticidal activity. These compounds are represented by formula (I): R Preferred are those compounds of formula (I) where $R^2$ and R3 taken together is $=NCH(R^6)CH(R^7)N(R^8)-$, $=NC(R6)=C(R7)N(R8)-$, or $=CHN=C(R^7)N(R^8)-$, and tautomers thereof, and where $R^4$ and $R^5$ taken together is $-C(R11)=C(R12)C(R13)=C(R14)$ 1 12, -, where R, R, R6, R7, R8, RI1, R R13, R14, and X are described. In addition, compositions comprising an insecticidally effective amount of at least one compound of formula (I), and optionally, an effective amount of at least one of a second compound with at least one insecticidally compatable carrier are also disclosed; along with methods of controlling insects comprising applying said compositions to a locus where insects are present or are expected to be present.

(I)

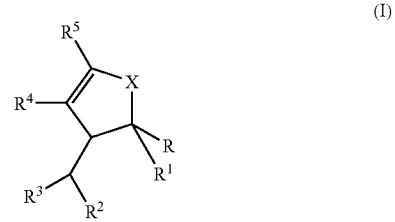

10 Claims, No Drawings

PESTICIDAL HETEROCYCLES

This Application is a divisional of U.S. application Ser. No. 10/512,377, filed Oct. 25, 2004 which is a 35 U.S.C. §371 U.S. National Phase filing of International Application No. PCT/US03/13127, filed Apr. 28, 2003, which claims benefit of U.S. Provisional Application 60/376,363, filed Apr. 29, 2002. The entirety of each of these applications is herein incorporated by reference.

FIELD OF THE INVENTION

The present invention generally relates to pesticidal compounds and their use in controlling pests. In particular, it pertains to insecticidal and acaricidal heterocyclic derivatives and agriculturally acceptable salts thereof, compositions of these pesticides, and methods for their use in controlling pests.

BACKGROUND OF THE INVENTION

It is well known that pests such as insects and acarids can cause significant damage to crops grown in agriculture, resulting in loss of millions of dollars of value associated with a given crop.

Although there are many orders of insects that can cause significant crop damage, insects, for example, of the suborder "Homoptera" are of major importance. The suborder Homoptera includes, for example, aphids, leafhoppers, cicadas, whiteflies, and mealybugs, to name a few. Homopterans have piercing/sucking mouthparts, enabling them to feed by withdrawing sap from vascular plants. Insect damage from homopterans is manifested in several different ways, other than damage caused by direct feeding. For example, many species excrete honeydew, a sticky waste product that adheres to plants upon which the insect feeds and lives. Honeydew alone causes cosmetic injury to crop plants. Sooty molds will often grow on honeydew, making food products or ornamental plants look unappealing, thereby reducing their cosmetic and economic value. Some homopterans have toxic saliva that is injected into plants while they are feeding. The saliva can cause plant damage through disfigurement and in some instances plant death. Homopterans can also vector disease-causing pathogens. Unlike direct damage, it does not take a large number of disease-vectoring insects to cause considerable damage to crop plants.

Acarids, for example, the two-spotted spider mite and the bean spider mite are serious pests for many vegetable crops including tomatoes, beans and cucurbits. These mites, as well as other acarids also cause damage to a wide variety of other vegetables, fruits and ornamental plants all over the world. Spider mites cause serious economic damage to vegetable crops by feeding on foliage, the effect of which is to reduce photosynthesis, transpiration, leaf chlorophyll content and leaf nitrogen, and increase transpiration. Mite feeding can reduce bud formation and fruit size, as well as cause poor fruit finish and color development.

Accordingly, there is a continuing demand for new insecticides for control of, for example, Homoptera and other orders of insects; as well as new acaricides, that are safer, more effective, and less costly for use on crops such as those set forth above, and also for use on wheat, corn, soybeans, potatoes, and cotton to name a few. For crop protection, insecticides and acaricides are desired which can control the insects and acarids without damaging the crops, and have no deleterious effects to mammals and other living organisms.

A paper presented by Dow AgroSciences at the 220th meeting of the American Chemical Society in 2000, entitled 'Restricted Analog Design Strategies of Arylalkylimidazole Insecticides" discloses a class of imidazoles having insecticidal activity against cotton aphid, of which the following is an example:

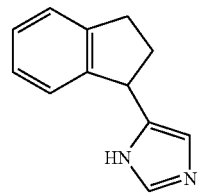

A paper presented in the Journal of Medicinal Chemistry (1986, 29, 463-467) discloses a class of imidazoline derivatives, of the following structure, having biological effects at $\alpha_1$ and $\alpha_2$ adrenergic receptors:

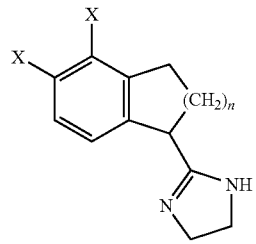

where X is hydroxy, or methoxy, and n is 0 to 3. There is no disclosure or suggestion that any of the adrenergic receptors have insecticidal activity.

SUMMARY OF THE INVENTION

In accordance with the present invention, it has now been found that certain novel heterocyclic derivatives and agriculturally acceptable salts thereof are useful as active ingredients in insecticidal compositions and methods of this invention. These compounds are represented by the following general formula I:

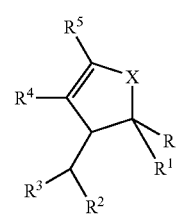

where R, $R^1$, $R^2$, $R^3$, $R^4$, $R^5$ and X are fully described below. Among the preferred compounds are those where $R^2$ and $R^3$ are taken together to form a five- or six-membered ring, and are =NCH($R^6$)CH($R^7$)N($R^8$)—, =NC($R^6$)=C($R^7$)N($R^8$)—, and =CHN=C($R^7$)N($R^8$)—; $R^4$ and $R^5$ are taken together to form a fused ring, and is —C($R^{11}$)=C($R^{12}$)C($R^{13}$)=C($R^{14}$)—; and X is selected from —CHR$^{17}$—, —CH$_2$CHR$^{17}$—, —OCH$_2$—, and —SCH$_2$—; where $R^6$, $R^7$, $R^8$, $R^{11}$, $R^{12}$, $R^{13}$, $R^{14}$ and $R^{17}$ are also fully described below.

The present invention is also directed to compositions containing an insecticidally effective amount of at least one of a compound of formula I, and optionally, an effective amount of at least one of a second compound, with at least one insecticidally compatible carrier.

The present invention is also directed to methods of controlling insects, where control is desired, which comprise applying an insecticidally effective amount of the above composition to the locus of crops, or other areas where insects are present or are expected to be present.

DETAILED DESCRIPTION OF THE INVENTION

One aspect of the present invention relates to certain new and useful compounds, namely certain novel heterocyclic derivatives as depicted in general formula I:

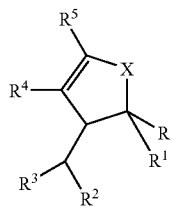

I

Wherein
—R and $R^1$ are independently selected from hydrogen and alkyl;
—$R^2$ and $R^3$ are taken together to form a five- or six-membered ring selected from =NCH($R^6$)CH($R^7$)N($R^8$)—, =NC($R^6$)=C($R^7$)N($R^8$)—, =CHC($R^6$)=C($R^7$)N($R^8$)—, =CHN=C($R^7$)N($R^8$)—, =N(CH$_2$)$_3$N($R^8$)—, =NCH($R^6$)CH($R^7$)S—, =NCH($R^6$)CH($R^7$)O—, =CHCH=CHCH=N—, =NN=CHN($R^8$)—, =NN=NN($R^8$)—, —OCH($R^6$)CH($R^7$)N($R^8$)N=, and tautomers thereof;
where
$R^6$ and $R^7$ are independently selected from hydrogen and alkyl;
$R^8$ is selected from hydrogen, alkyl, amino, nitro, cyano, formyl, —CH$_2$R$^9$—, —CH$_2$OR$^9$, —C(O)R$^9$, —C(O)OR$^9$, —CH$_2$OC(O)R$^9$, —C(O)N(R$^9$)(R$^{10}$), —S(O)$_n$R$^9$—, —S(O)$_n$N(R$^9$)(R$^{10}$) where n is 0, 1, or 2, —Si(R$^9$)$_3$, —CH=N(R$^9$), —P(O)(OR$^9$)(OR$^{10}$), —P(O)(NR$^9$R$^{10}$)(NR$^9$R$^{10}$), and Y, wherein Y represents i) an N-oxide of said five- or six-membered ring, or ii) forms an OR$^a$ linkage wherein R$^a$ is selected from hydrogen and alkyl; and,
$R^9$ and $R^{10}$ are independently selected from hydrogen, alkyl, alkylcarbonyl, alkoxycarbonyl aryl, arylalkyl, and heteroaryl, wherein aryl is optionally substituted with one or more substituent independently selected from halogen, alkyl, or haloalkyl;
—$R^4$ and $R^5$ are taken together to form a fused ring selected from —C(R$^{11}$)=C(R$^{12}$)C(R$^{13}$)=C(R$^{14}$)—, —SC(R$^{15}$)=C(R$^{16}$)—, —C(R$^{15}$)=C(R$^{16}$)S—, and —CH=C(R$^{15}$)N=CH—,
where
$R^{11}$ and $R^{14}$ are independently selected from hydrogen, halogen, and methyl;
$R^{12}$ is selected from hydrogen, halogen, amino, (C$_1$-C$_2$)alkyl, methoxy, halomethoxy, (C$_2$-C$_3$)alkenyl, and (C$_2$-C$_3$)alkynyl;

$R^{13}$ is selected from hydrogen, halogen, cyano, (C$_1$-C$_2$)alkyl, hydroxy, methoxy, halomethyl, and (C$_2$-C$_3$)alkynyl;
and,
$R^{15}$ and $R^{16}$ are independently selected from hydrogen, halogen, cyano, amino, (C$_1$-C$_2$)alkyl, (C$_2$-C$_3$)alkenyl, (C$_2$-C$_3$)alkynyl halomethyl, hydroxy, methoxy, and halomethoxy;
—X is selected from —CHR$^{17}$—, —CH$_2$CHR$^{17}$—, —C$_3$H$_6$—, —C$_4$H$_8$—, —O—, —OCH$_2$—, —OC$_2$H$_4$—, —OC$_3$H$_6$—, —CH$_2$O—, —CH$_2$OCH$_2$—, —CH$_2$OC$_2$H$_4$—, —S—, —SCH$_2$—, —CH$_2$S—, —CH$_2$S(O)—, —CH$_2$S(O)$_2$—, —N(R$^{17}$)CH$_2$—; and —CH$_2$N(R$^{17}$)—;
where
$R^{17}$ is selected from hydrogen and alkyl; and
agriculturally-acceptable salts thereof;
with the proviso that when R and $R^1$ are hydrogen; $R^2$ and $R^3$ taken together is =CHN=C(R$^7$)N(R$^8$)—, where $R^7$ and $R^8$ are hydrogen; $R^4$ and $R^5$ taken together is —C(R$^{11}$)=C(R$^{12}$)C(R$^{13}$)=C(R$^{14}$)—; and X is —CHR$^{17}$, where $R^{17}$ is hydrogen; then at least one of $R^{11}$, $R^{12}$, $R^{13}$, or $R^{14}$ is other than hydrogen; and,
with the further proviso that when R and $R^1$ are hydrogen; $R^2$ and $R^3$ taken together is =NCH(R$^6$)CH(R$^7$)N(R$^8$)—; where $R^6$, $R^7$, and $R^8$ are hydrogen; $R^4$ and $R^5$ taken together is —C(R$^{11}$)=C(R$^{12}$)C(R$^{13}$)=C(R$^{14}$)—, and X is —CHR$^{17}$, where $R^{17}$ is hydrogen; then i) when $R^{11}$, $R^{13}$ and $R^{14}$ are hydrogen, then $R^{12}$ is other than methyl; ii) when $R^{11}$ is hydrogen, $R^{13}$ is methyl, and $R^{14}$ is bromo, then $R^{12}$ is other than hydrogen; iii) when $R^{11}$ and $R^{14}$ are hydrogen, and $R^{12}$ is methoxy, then $R^{13}$ is other than methoxy, and iv) when X is —CH$_2$CHR$^{17}$—, or —OCH$_2$—; $R^{17}$ is hydrogen; $R^{11}$ and $R^{14}$ are hydrogen, $R^{12}$ is methoxy, and $R^{13}$ is methyl; then $R^8$ is other than —S(O)$_n$R$^9$, where n is 2, and $R^9$ is methyl.

Excluding those compounds set forth in the provisos above, preferred species are those compounds of formula I where $R^2$ and $R^3$ taken together is =NCH(R$^6$)CH(R$^7$)N(R$^8$)—, =NC(R$^6$)=C(R$^7$)N(R$^8$)—, or =CHN=C(R$^7$)N(R$^8$)—, and tautomers thereof, where $R^8$ is selected from hydrogen, cyano, —S(O)$_n$N(R$^9$)(R$^{10}$), and —P(O)(OR$^9$)(OR$^{10}$), where n is 2, and $R^9$ and $R^{10}$ are independently selected from hydrogen and alkyl; $R^4$ and $R^5$ are taken together to form a fused ring, where $R^4$ and $R^5$ together is —C(R$^{11}$)=C(R$^{12}$)C(R$^{13}$)=C(R$^{14}$), where $R^{11}$ is hydrogen, $R^{12}$ is selected from halogen and methoxy, and $R^{13}$ is selected from halogen and (C$_1$-C$_2$) alkyl; and, X is selected from —CHR$^{17}$—, —CH$_2$CHR$^{17}$—, —OCH$_2$—, and —SCH$_2$—. Particularly preferred are those compounds where $R^9$ and $R^{10}$ are each methyl; $R^{12}$ is selected from chlorine and methoxy; $R^{13}$ is selected from chlorine and methyl; and, $R^{14}$ is selected from hydrogen, chlorine and methyl; and X is selected from —CH$_2$CHR$^{17}$— and —OCH$_2$—, where $R^{17}$ is hydrogen.

In addition, in certain cases the compounds of the present invention may possess asymmetric centers, which can give rise to optical enantiomorphs and diastereomers. The compounds may exist in two or more forms, i.e., polymorphs, which are significantly different in physical and chemical properties. The compounds of the present invention may also exist as tautomers, in which migration of a hydrogen atom within the molecule results in two or more structures, which are in equilibrium, for example Compounds 256-278 of the present invention. The compounds of the present invention may also possess acidic or basic moieties, which may allow for the formation of agriculturally acceptable salts or agriculturally acceptable metal complexes.

This invention includes the use of such enantiomorphs, polymorphs, tautomers, salts and metal complexes. Agriculturally acceptable salts and metal complexes include, without limitation, for example, ammonium salts, the salts of organic and inorganic acids, such as hydrochloric acid, sulfonic acid, ethanesulfonic acid, trifluoroacetic acid, methylbenzenesulfonic acid, phosphoric acid, gluconic acid, pamoic acid, and other acid salts, and the alkali metal and alkaline earth metal complexes with, for example, sodium, potassium, lithium, magnesium, calcium, and other metals.

Another aspect of the present invention relates to compositions containing an insecticidally effective amount of at least one compound of formula I with at least one insecticidally compatible carrier therefor.

Another aspect of the present invention relates to compositions containing an insecticidally effective amount of at least one compound of formula I, and an effective amount of at least one second compound, with at least one insecticidally compatible carrier therefor.

Another aspect of the present invention relates to methods of controlling insects by applying an insecticidally effective amount of a composition set forth above to a locus of crops such as, without limitation, cereals, cotton, vegetables, and fruits, or other areas where insects are present or are expected to be present.

The present invention also includes the use of the compounds and compositions set forth herein for control of non-agricultural insect species, for example, dry wood termites and subterranean termites; as well as for use as pharmaceutical agents and compositions thereof.

As used in this specification and unless otherwise indicated the substituent terms "alkyl" and "alkoxy", used alone or as part of a larger moiety, includes straight or branched chains of at least one or two carbon atoms, as appropriate to the substituent, and preferably up to 12 carbon atoms, more preferably up to ten carbon atoms, most preferably up to seven carbon atoms. The term "alkenyl" and "alkynyl" used alone or as part of a larger moiety, includes straight or branched chains of at least two carbon atoms containing at least one carbon-carbon double bond or triple bond, and preferably up to 12 carbon atoms, more preferably up to ten carbon atoms, most preferably up to seven carbon atoms. The term "aryl" refers to an aromatic ring structure, including fused rings, having four to ten carbon atoms, for example, phenyl or naphthyl. The term "heteroaryl" refers to an aromatic ring structure, including fused rings, in which at least one of the atoms is other than carbon, for example, without limitation, sulfur, oxygen, or nitrogen. The term "GC analysis" refers to gas chromatographic analysis of, for example, a reaction mixture. The term "DMF" refers to N,N-dimethylformamide. The term "THF" refers to tetrahydrofuran. The term "halogen" or "halo" refers to fluorine, bromine, iodine, or chlorine. The term "hyperactivity" or "insect hyperactivity" refers to an abnormal physical state of an insect, for example, a cotton aphid, where the insect walks excessively thereby removing itself from, for example, a crop plant. The term "ambient temperature" or "room temperature" often abbreviated as "RT", for example, in reference to a chemical reaction mixture temperature, refers to a temperature in the range of 20° C. to 30° C. The term "pesticidal" or "pesticide" refers to a compound of the present invention, either alone or in admixture with at least one of a second compound, or with at least one compatible carrier, which causes the destruction or the inhibition of action of insects or acarids, or insects and acarids.

The heterocyclic derivatives of formula I can be synthesized by methods that are individually known to one skilled in the art from intermediate compounds readily available in commerce. Scheme I below illustrates a general procedure for synthesizing heterocyclic derivatives of formula I, inter alia, where, for example, R and $R^1$ are hydrogen; $R^2$ and $R^3$ taken together is =NCH($R^6$)CH($R^7$)N($R^8$)—; $R^4$ and $R^5$ taken together is —C($R^{11}$)=C($R^{12}$)C($R^{13}$)=C($R^{14}$)—; and X is —CHR$^{17}$—, CH$_2$CHR$^{17}$—, —OCH$_2$— or —SCH$_2$— where $R^6$, $R^7$, $R^8$, and $R^{17}$ are hydrogen:

SCHEME I

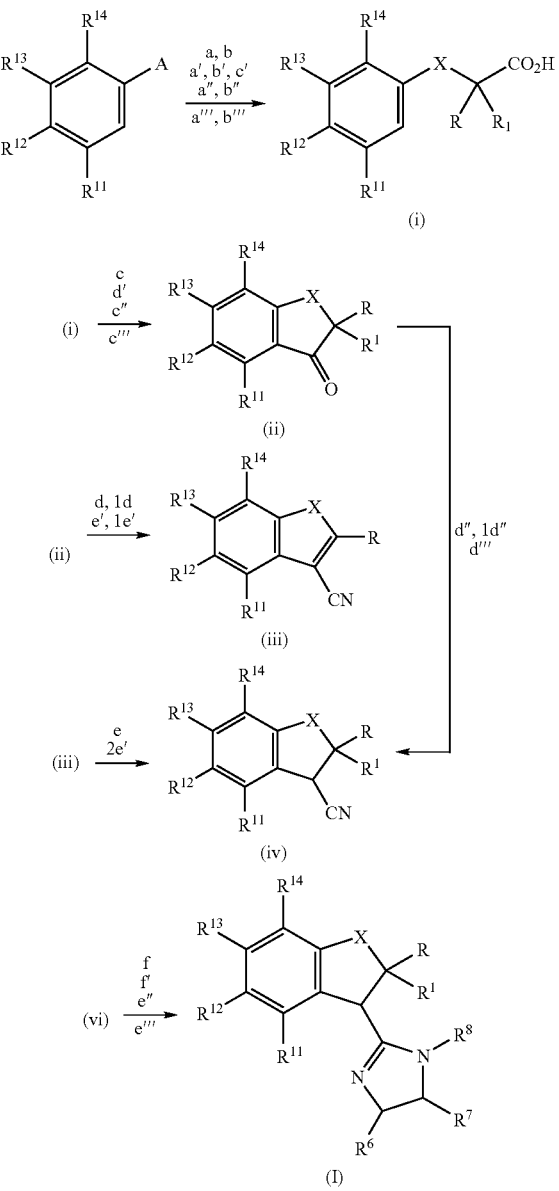

Where X is —CHR$^{17}$— or —CH$_2$CHR$^{17}$—, A is Br.
Where X is —OCH$_2$—, A is OH. Where X is —SCH$_2$—, A is SH.

Where X is —CHR$^{17}$— follows Step a through Step f:
a) n-BuLi/THF/DMF/-60° C. to -70° C. (Converts A = —Br to —CHO);
b) 2, 2-dimethyl-1-1, 3-dioxane-4, 6-dione/HCOOH/Et$_3$N/-5° C. to 95° C. (Converts —CHO to Intermediate (i)); c) Eaton's Reagent/39° C. (Converts Intermediate (i) to Intermediate ii)); d) N≡CP(O)(OC$_2$h$_5$)$_2$/LiCN/THF; 1d) BF$_3$—O(C$_2$H$_5$)$_2$/Toluene/ 45° C. (d, and 1d converts Intermediate (ii) to Intermediate (iii)); e) H$_2$/10% Pd on carbon/10% Pt on carbon/EtOAc (Converts Intermediate (iii) to Intermediate (iv)); f) p-CH$_3$C$_6$H$_4$SO$_3^-$NH$_3^+$CH$_2$CH$_2$NH$_2$/140° C.-160° C. (Converts Intermediate (iv) to a Compound of Formula (I)).

-continued

Where X is —CH$_2$CHR$^{17}$ follows Step a' through Step f':
a') —CCH$_2$CH$_2$OH/[(C$_6$H$_5$)$_3$P]$_2$PdCl$_2$/90° C. (Converts A = —Br to —C≡CCH$_2$CH$_2$OH); b) H$_2$/10% Pd on carbon/CH$_3$OH (Converts —C≡CCH$_2$CH$_2$OH to —CH$_2$CH$_2$CH$_2$OH); c') Jones' Reagent/Acetone/0° C. to RT (Converts —CH$_2$CH$_2$CH$_2$OH to Intermediate (i)); d') Eaton's Reagent/ RT (Converts Converts Intermediate (i) to Intermediate (ii)); e') (CH$_3$)$_3$SiCN/AlCl$_3$/ Toluene/70° C. (Converts Intermediate (ii) to a silaethoxy intermediate); 1e') (CH$_3$)$_3$SiCl/NaI/CH$_3$CN/H$_2$O/RT (Converts cyano-silyl intermediate to a mixture of Intermediate (iii) and Intermediate (iv)); 2e') H$_2$/10% Pd on carbon/10% Pt on carbon/ EtOAc (Converts mixture of Intermediate (iii) and Intermediate (iv) to Intermediate (iv); f') p-CH$_3$C$_6$H$_4$SO$_3$-NH$_3$+CH$_2$CH$_2$NH$_2$/140° C.-180° C. (Converts Intermediate (iv) to a Compound of Formula (I)).
Where X is —OCH$_2$— follows Step a" through Step e";
a") ClCH$_2$CH$_2$CH$_2$OH/Aq. 10% NaOH/Reflux (Converts A = —OH to OCH$_2$CH$_2$CH$_2$OH); or CH$_2$=CH$_2$CN/Triton® B/reflux (Converts A = OH to OCH$_2$CH$_2$CN; b") Jones' Reagent/Acetone/5° C. to 10° C. (Converts OCH$_2$CH$_2$CH$_2$OH to Intermediate (i)), or Conc. HCl/reflux (Converts OCH$_2$CH$_2$CN to Intermediate (i)); c") Oxalyl chloride/AlCl$_3$DMF/CH$_2$Cl$_2$/5° C. to RT (Converts Intermediate (i) to Intermediate (ii)); d") (CH$_3$)$_3$SiCN/AlCl$_3$/Toluene/70° C. (Converts Intermediate (ii) to a silaethoxy intermediate); 1d") (CH$_3$)$_3$SiCl/NaI/CH$_3$CN/H$_2$O/RT (Converts cyano-silyl intermediate to Intermediate (iv)); e") p-CH$_3$C$_6$H$_4$SO$_3$-NH$_3$+CH$_2$CH$_2$NH$_2$/140° C. (Converts Intermediate (iv) to a Compound of Formula (I)).
Where X is —SCH$_2$— follows Step a''' through Step e''';
BrCH$_2$CH$_2$CO$_2$CH$_3$/DMF (Converts A = -SH to —SCH$_2$CH$_2$CO$_2$CH$_3$); b''') Aq. 10% KOH/CH$_3$OH (Converts —SCH$_2$CH$_2$CO$_2$CH$_3$ to Intermediate (i)); c''') Oxalyl chloride/AlCl$_3$/DMF/CH$_2$Cl$_2$/5° C. to RT (Converts Intermediate (i) to Intermediate (ii)); d''') 1-(CH$_3$)$_3$SiCN/AlCl$_3$/Toluene/70° C., 2-(CH$_3$)$_3$SiCl/NaI/CH$_3$CN/H$_2$O/RT (Converts Intermediate (ii) to Intermediate (iv)); e''') r-CH$_3$C$_6$H$_4$SO$_3$-NH$_3$+CH$_2$CH$_2$NH$_2$/140° C. (Converts Intermediate (iv) to a Compound of Formula (I)).

The heterocyclic ring where R$^2$ and R$^3$ taken together is =NCH(R$^6$)CH(R$^7$)N(R$^8$)—, as shown in Schema I, represents one tautomeric form in which this moiety can exist.

In a first step as set forth in Scheme I, an appropriate carboxylic acid (Intermediate (i)) was prepared. The synthetic route by which the carboxylic acid (i) was prepared depends upon what the moiety X is. For example, where X is —CHR$^{17}$—, an appropriately substituted phenyl bromide, such as 5-bromo-2-methoxytoluene, was lithiated at reduced temperature, and then was treated with DMF in an appropriate solvent, affording the corresponding aldehyde derivative. The aldehyde derivative was in turn condensed at elevated temperature with 2,2-dimethyl-1, 3-dioxane-4,6-dione, then decarboxylated and reduced with triethylamine-formic acid salt, yielding the corresponding carboxylic acid (i). When X is —CH$_2$CHR$^{17}$—, an appropriately substituted phenyl bromide was reacted at elevated temperature with an appropriate alkynyl alcohol, such as 3-butyn-1-ol, copper(I) iodide, and triethylamine, in the presence of a catalyst in an appropriate solvent, affording the corresponding phenyl-substituted alkynyl alcohol. The so-prepared alkynyl alcohol was then hydrogenated in the presence of a catalytic amount of 10% palladium on carbon in an appropriate solvent, affording the corresponding phenyl-substituted alkyl alcohol, which was in turn treated with Jones Reagent, thereby providing the corresponding carboxylic acid (i). When X is —OCH$_2$— or —SCH$_2$—, an appropriately substituted phenol or thiophenol, for example, 3-methylphenol or 3-methylthiophenol was reacted with a haloalkyl alcohol or a haloalkyl ester under basic conditions, yielding the corresponding phenoxyalkyl alcohol or the phenylthioalkyl ester. The phenoxyalkyl alcohol was then treated with Jones Reagent and the phenylthioalkyl ester was treated with a strong base, affording the corresponding carboxylic acid (i). In an alternate method, where X is —OCH$_2$—, an appropriately substituted phenol, for example, 3-methyl-4-methoxyphenol was reacted with acrylonitrile in the presence of a base, affording the corresponding propanenitrile, for example, 3-(4-methoxy-3-methylphenoxy)propanenitrile. The propanenitrile was then treated with concentrated hydrochloric acid, yielding the corresponding carboxylic acid (i).

In a second step as depicted in Scheme I, when X is —CHR$^{17}$—, or —CH$_2$CHR$^{17}$—, the carboxylic acids (i) were then converted to cyclic ketones (Intermediate (ii)) by treatment with Eaton's Reagent, yielding, for example, 6-methoxy-5-methylindan-1-one (X is —CHR$^{17}$—), or 7-methoxy-6-methyl-2,3,4-trihydronaphthalen-1-one (X is —CH$_2$CHR$^{17}$—). When X is —OCH$_2$—, the carboxylic acid (i) was first converted to the corresponding acid halide at reduced temperature in an appropriate solvent, which was then treated with aluminum chloride, affording the corresponding cyclic ketone (ii), for example, 7-methylchroman-4-one.

In a third step as depicted in Scheme I, the cyclic ketones (ii) were then converted a) directly to an unsaturated nitrile (Intermediate (iii)), b) directly to a saturated nitrile (Intermediate (iv)), or c) to mixtures of (iii) and (iv). When X is —CHR$^{17}$—, the cyclic ketone (ii), for example, 6-methoxy-5-methylindan-1-one, was reacted with lithium cyanide and diethyl cyanophosphonate at elevated temperature, then treated with boron trifluoride diethyl etherate in an appropriate solvent, yielding the corresponding unsaturated nitrile (iii), for example, 5-methoxy-6-methylinden-3-carbonitrile. Using an alternate method when X is —CH$_2$CHR$^{17}$—, the cyclic ketone (ii), for example, 7-methoxy-6-methyl-2,3,4-trihydronaphthalen-1-one, was reacted with trimethylsilyl cyanide in the presence of a catalytic amount of aluminum chloride at elevated temperature, affording a silaethoxy intermediate. The silaethoxy intermediate was then treated with sodium iodide, trimethylsilyl chloride, and water in an appropriate solvent, yielding a corresponding mixture of unsaturated nitrile (iii), and saturated nitrile (iv); for example, a mixture of 7-methoxy-6-methyl-3,4-dihydronaphthalenecarbonitrile and 7-methoxy-6-methyl-1,2,3,4-tetrahydronaphthalenecarbonitrile, respectively. When X is —OCH$_2$— or —SCH$_2$—, the cyclic ketone (ii), for example, 7-methylchroman-4-one or 7-methyl-2H,3H-benzo[e]thiin-4-one, was also reacted with trimethylsilyl cyanide in the presence of a catalytic amount of aluminum chloride, then treated with sodium iodide, trimethylsilyl chloride, and water in an appropriate solvent, directly yielding the corresponding saturated nitrile (iv); for example, 7-methylchromane-4-carbonitrile or 7-methyl-2H,3H-benzo[e]thiin-4-carbonitrile.

In a forth step as depicted in Scheme I, unsaturated nitriles (iii), and mixtures of unsaturated nitrile (iii) and saturated nitrile (iv), prepared as set forth above, were converted to saturated nitriles (iv) by hydrogenation in the presence of at least one catalyst, such as 10% platinum on carbon and/or 10% palladium on carbon, in an appropriate solvent.

In a fifth step as depicted in Scheme I, where R$^2$ and R$^3$ taken together is =NCH(R$^6$)CH(R$^7$)N(R$^8$)—; the saturated nitriles (iv) were converted to compounds of formula (I) by reaction of the saturated nitriles with the ethylenediamine salt of p-toluenesulfonic acid at elevated temperatures. Examples 1-3, 5 and 6 set forth below provide in detail those synthetic routes shown in Scheme I.

Scheme II below illustrates a general procedure for synthesizing yet other heterocyclic derivatives of formula I, inter alia, where, for example, R and R$^1$ are hydrogen; R$^2$ and R$^3$ taken together is =CHN=C(R$^7$)N(R$^8$)—; R$^4$ and R$^5$ taken together is —C(R$^{11}$)=C(R$^{12}$)C(R$^{13}$)=C(R$^{14}$)—; and X is —CHR$^{17}$—, CH$_2$CHR$^{17}$—, —OCH$_2$—, or —SCH$_2$— where R$^7$, R$^8$, and R$^{17}$ are hydrogen:

SCHEME II

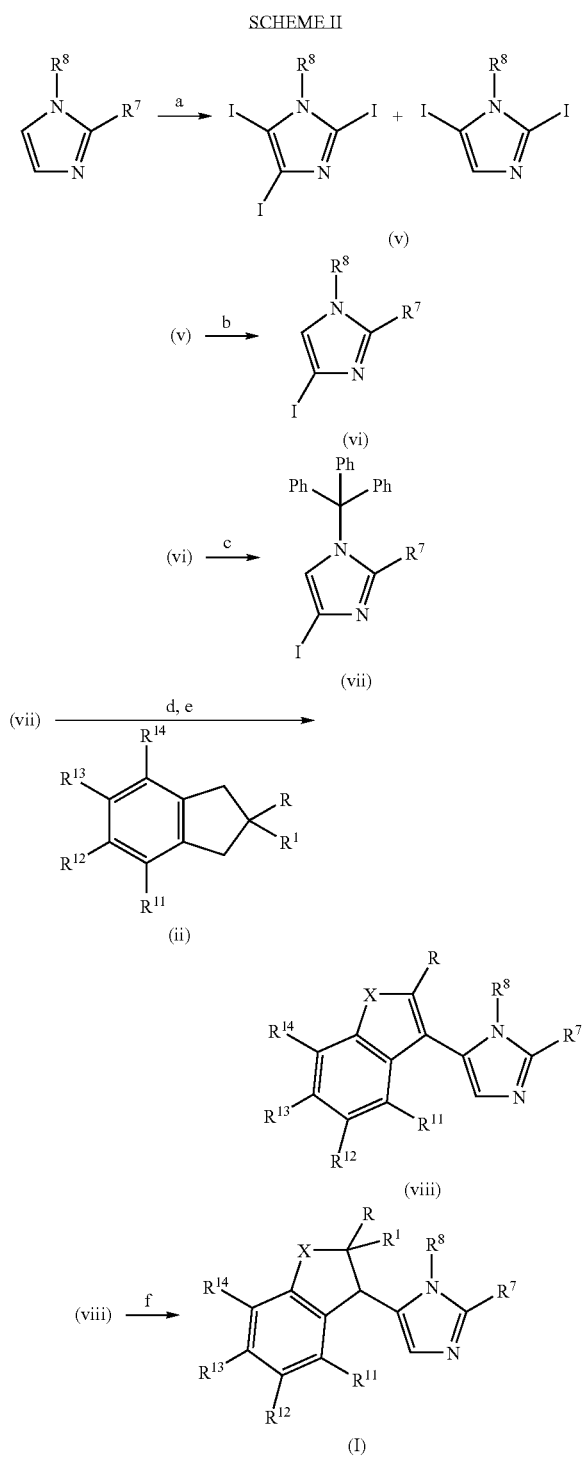

Where $R^7$ and $R^8$ are hydrogen Imidazole

Where X is —CHR$^{17}$—:
a) I$_2$/aq. 2N NaOH/CH$_2$Cl$_2$/10° C.; b) Na$_2$SO$_3$/H$_2$O/EtOH/Reflux; c) (Ph)$_3$CCl/Et$_3$N/DMF/RT; d) Intermediate (ii)/EtMgBr/CH$_2$Cl$_2$/21° C.; e) aq. HCl/CH$_3$OH; f) H$_2$/10% Pd on carbon/PtO$_2$-hydrate/EtOH/RT.

As set forth in Scheme II, the heterocyclic ring where $R^2$ and $R^3$ taken together is =CHN=C(R$^7$)N(R$^8$)— is synthesized prior to its reaction with a cyclic ketone (ii), yielding the corresponding intermediate (viii) penultimate to compounds of formula (I). The heterocyclic ring where $R^2$ and $R^3$ taken together is =CHN=C(R$^7$)N(R$^8$)—, as shown in Schema II represents one tautomeric form in which this moiety can exist.

As depicted in Scheme II, imidazole was reacted with iodine under basic conditions at reduced temperature in an appropriate solvent, yielding a mixture of iodoimidazoles (v), for example, 2,4,5-triiodoimidazole and 2,5-diiodoimidazole. The mixture of iodoimidazole derivatives (v) was then treated with aqueous sodium sulfite at elevated temperature in an appropriate solvent, yielding a single iodo derivative (vi), for example, 5-iodoimidazole. The free amine in the 1-position of the iodoimidazole (vi) ring was then protected by reacting it with triphenylmethyl chloride under basic conditions in an appropriate solvent, affording the corresponding 1-(triphenylmethyl)-4-iodoimidazole (vii). The iodoimidazole (vii) was in turn treated with ethylmagnesium bromide in an appropriate solvent, then reacted with an appropriate cyclic ketone (ii), for example, 6-methoxy-5-methylindan-1-one (X is —CHR$^{17}$—), affording the corresponding 1,2-unsaturated heterocyclic derivative (viii), for example, 3-(imidazol-5-yl)-5-methoxy-6-methylindene. Heterocyclic derivative (viii) was then hydrogenated under conditions set forth above, yielding the corresponding compounds of formula (I), for example, 1-(imidazol-5-yl)-6-methoxy-5-methylindane. Example 4 set forth below provides in detail the synthesis route shown in Scheme II.

Scheme III below illustrates a general procedure for synthesizing yet other heterocyclic derivatives of formula I, inter alia, where, for example, R and $R^1$ are hydrogen; $R^2$ and $R^3$ taken together is =CHN(R$^8$)C(R$^7$)=N—; $R^4$ and $R^5$ taken together is —C(R$^{11}$)=C(R$^{12}$)C(R$^{13}$)=C(R$^{14}$)—; and X is —CHR$^{17}$—, CH$_2$CHR$^{17}$—, —OCH$_2$—, or —SCH$_2$— where $R^7$ and $R^{17}$ are hydrogen, and $R^8$ is a substituent other than hydrogen:

SCHEME III

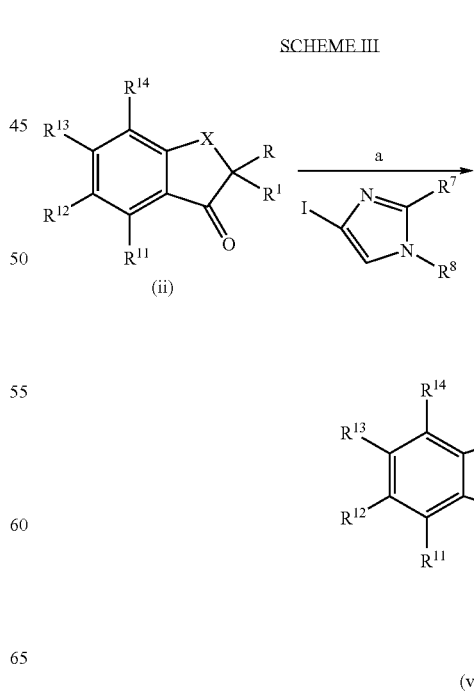

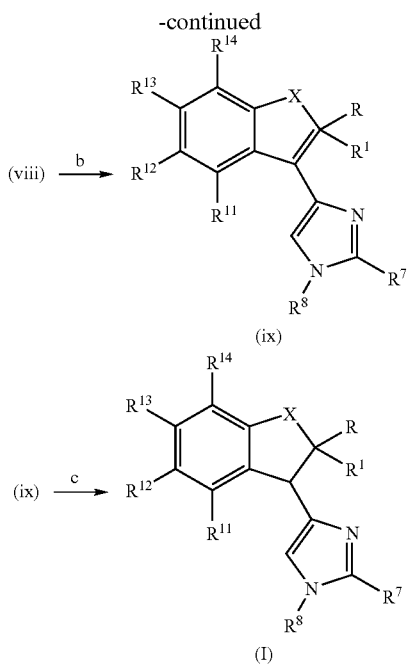

Where R[8] is, for example, —SO$_2$N(CH$_3$)$_2$ (Commercially Available)

Where X is —OCH$_2$—:
a) C$_2$H$_5$MgBr/CH$_2$Cl$_2$; b) CF$_3$CO$_2$H; c) 5% Pt on carbon/10% Pd on carbon/CH$_3$OH As set forth in Scheme III, the iodo analog of the heterocyclic ring where R[2] and R[3] are taken together is =CHN(R[8])C(R[7])=N—, where R[7] is hydrogen and R[8] is, for example, —SO$_2$N(CH$_3$)$_2$ is commercially available. The heterocyclic ring where R[2] and R[3] taken together is =CHN(R[8])C(R[7])=N—, as shown in Schema III represents one tautomeric form in which this moiety can exist. The iodo-substituted heterocyclic rings, such as that set forth above can be reacted with intermediates previously described to prepare additional compounds of formula (I).

As depicted in Scheme III, intermediate (ii), previously described, for example, 6-methoxy-7-methylchroman-4-one, was reacted with the Grignard Reagent prepared from treatment of the iodo analog of the heterocyclic ring, for example, [(4-iodoimidazolyl)sulfonyl]dimethylamine, with ethylmagnesium bromide, affording the corresponding 4-hydroxy intermediate (viii), for example, {[4-(4-hydroxy-6-methoxy-7-methylchroman-4-yl)imidazolyl]sulfonyl}dimethylamine. The hydroxy intermediate (viii) was then dehydrated with a dehydrating agent, for example, trifluoroacetic acid, yielding the corresponding unsaturated intermediate (ix), for example, {[4-(6-Methoxy-7-methyl(2H-chromen-4-yl)imidazolyl]sulfonyl}dimethylamine. Lastly, intermediate (ix) was reduced with hydrogen gas in the presence of appropriate catalysts, for example, 10% palladium on carbon and 5% platinum on carbon, in an appropriate solvent, yielding a compound of formula (I), for example, {[4-(6-methoxy-7-methylchroman-4-yl)imidazolyl]sulfonyl}dimethylamine. Example 7 set forth below provides in detail the synthesis route shown in Scheme III.

Scheme IV below illustrates a general procedure for synthesizing yet other heterocyclic derivatives of formula I, inter alia, where, for example, R and R[1] are hydrogen; R[2] and R[3] taken together is =NC(R[6])=C(R[7])N(R[8])—; R[4] and R[5] taken together is —C(R[11])=C(R[12])C(R[13])=C(R[14])—; and X is —CHR[17]—, CH$_2$CHR[17]—, —OCH$_2$—, or —SCH$_2$— where R[6], R[7], R[8] and R[17] are hydrogen:

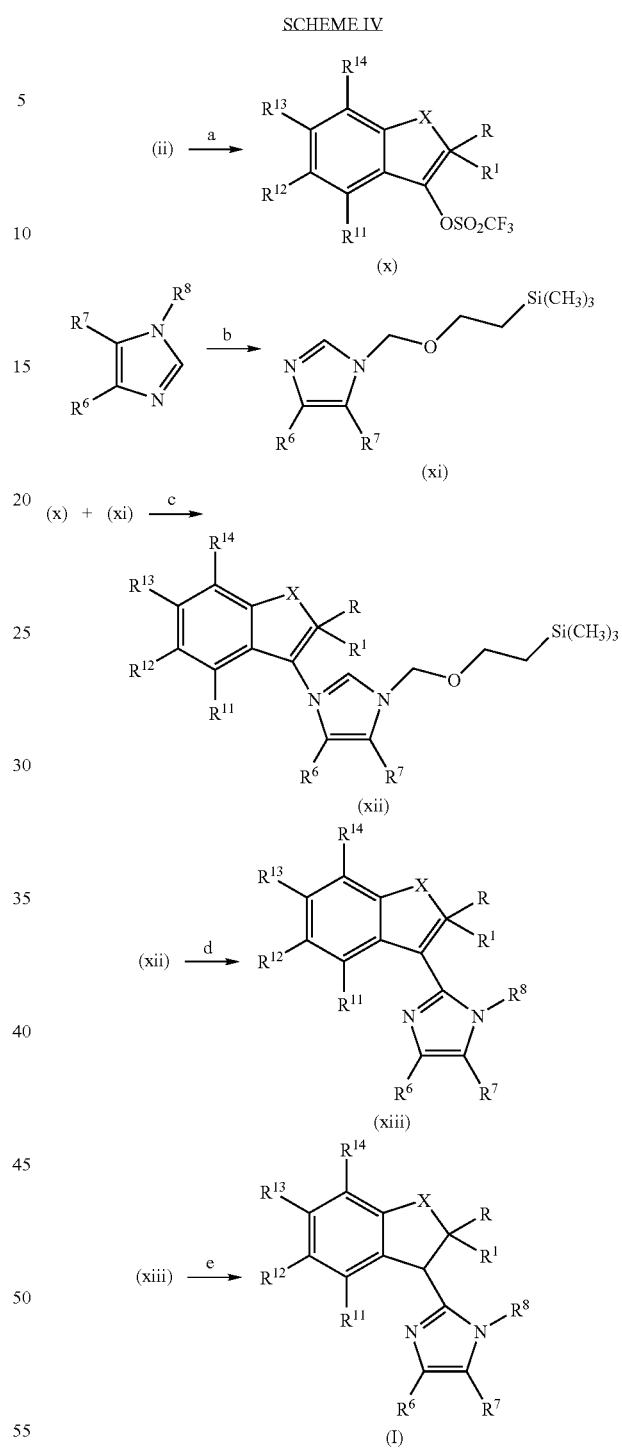

Where R[8] is hydrogen Imidazole

Where X is —CH$_2$CR[17]—:
a) LHMDS/(CF$_3$SO$_2$)$_2$NC$_6$H$_5$/THF; b) 60% NaH/ClCH$_2$OCH$_2$CH$_2$Si(CH$_3$)$_3$/THF/0-5° C.; c) 1-(xi)/n-BuLi/THF, 2-ZnCl$_2$/(C$_2$H$_5$)$_2$O/-78° C., 3-(x)/Pd[(PPh$_3$)]4/-78° C. to 60° C.; d) Conc. HCl; e) H$_2$PtO/10% Pd on carbon/C$_2$H$_5$OH As set forth in Scheme IV, the heterocyclic ring where R[2] and R[3] taken together is =NC(R[6])=C(R[7])N(R[8])— was coupled with, for example, a trifluoromethanesulfonyloxy derivative of a cyclic ketone (ii), wherein the R[8] position is protected by a leaving group, such as CH$_2$OCH$_2$CH$_2$Si(CH$_3$)$_3$, affording, in a step-wise manner, compounds of formula (I).

As depicted in Scheme IV, intermediate (ii), previously described, for example, 7-methoxy-6-methyl-2,3,4-trihydronaphthalen-1-one, was treated with lithium hexamethyldisilazane, then reacted with N-phenyltrifluoromethanesulfonimide in an appropriate solvent, yielding a trifluoromethanesulfonyloxy intermediate (x), for example, 7-methoxy-6-methyl-3,4-dihydronaphthyl (trifluoromethyl) sulfonate. As a separate reaction, an intermediate where $R^2$ and $R^3$ taken together is $=NC(R^6)=C(R^7)N(R^8)-$, such as imidazole, was treated with, for example, sodium hydride, then reacted with 2-(trimethylsilyl)ethoxymethyl chloride in an appropriate solvent, yielding the corresponding silabutane intermediate (xi) in which the $R^8$ position is protected. Intermediate (xi), for example, 1-(imidazolylmethoxy)-3,3-dimethyl-3-silabutane was then treated with 1) n-butyllithium, then 2) zinc chloride in an appropriate solvent; after which time intermediate (x) was introduced, along with a catalyst, such as tetrakis(triphenylphosphine)palladium(0), which yielded the appropriate silabutane intermediate (xii), for example, 1-{[2-(7-methoxy-6-methyl(3,4-dihydronaphthyl))imidazolyl]methoxy}-3,3-dimethyl-3-silabutane. The $R^8$ position of intermediate (xii) was then de-protected by reacting it with, for example, concentrated hydrochloric acid, yielding the corresponding intermediate wherein $R^8$ is hydrogen (xiii), for example, 4-imidazol-2-yl-6-methoxy-7-methyl-1,2-dihydronaphthalene. Intermediate (xiii) was then was reduced with hydrogen gas in the presence of appropriate catalysts, for example, 10% palladium on carbon and platinum oxide, in an appropriate solvent, yielding a compound of formula (I), for example, 1-imidazol-2-yl-7-methoxy-6-methyl-1,2,3,4-tetrahydronaphthaline. Example 8 set forth below provides in detail the synthesis route shown in Scheme IV.

Compounds of formula (I) of the present invention can be further reacted to provide additional compounds of formula (I). For example, those compounds of formula (I) wherein $R^8$ is hydrogen can be reacted with an appropriately substituted halide under basic conditions in an appropriate solvent, yielding compounds of formula (I) wherein $R^8$ is a substituent. In one method, for example, compounds of formula (I) were reacted with cyanogen bromide, or N,N-dimethylaminosulfonyl chloride, or chlorodimethylphosphate and N,N-diisopropylamine in an appropriate solvent, yielding compounds of formula (I) wherein $R^8$ is cyano, $-SO_2N(CH_3)_2$, or $-P(O)(OCH_3)_2$, respectively. Examples 9-11 set forth below provide in detail these syntheses routes.

The present invention also relates to insecticidal compositions that combine insecticidally effective amounts of the active compounds with adjuvants and carriers normally employed in the art for facilitating the dispersion of active ingredients for the particular utility desired. Such insecticidal compositions of the present invention include at least one of an insecticidally effective amount of a compound of formula I and at least one insecticidally compatible carrier therefor, wherein the compound of formula I is:

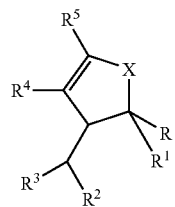

I wherein
—R and $R^1$ are independently selected from hydrogen and alkyl;

—$R^2$ and $R^3$ are taken together to form a five- or six-membered ring selected from $=NCH(R^6)CH(R^7)N(R^8)-$, $=NC(R^6)=C(R^7)N(R^8)-$, $=CHC(R^6)=C(R^7)N(R^8)-$, $=CHN=C(R^7)N(R^8)-$, $=N(CH_2)_3N(R^8)-$, $=NCH(R^6)CH(R^7)S-$, $=NCH(R^6)CH(R^7)O-$, $=CHCH=CHCH=N-$, $=NN=CHN(R^8)-$, $=NN=NN(R^8)-$, $-OCH(R^6)CH(R^7)N(R^8)N=$, and tautomers thereof;

where
$R^6$ and $R^7$ are independently selected from hydrogen and alkyl;
$R^8$ is selected from hydrogen, alkyl, amino, nitro, cyano, formyl, $-CH_2R^9-$, $-CH_2OR^9$, $-C(O)R^9$, $-C(O)OR^9$, $-CH_2OC(O)R^9$, $-C(O)N(R^9)(R^{10})$, $-S(O)_nR^9-$, $-S(O)_nN(R^9)(R^{10})$ where n is 0, 1, or 2, $-Si(R^9)_3$, $-CH=N(R^9)$, $-P(O)(OR^9)(OR^{10})$, $-P(O)(NR^9R^{10})(NR^9R^{10})$, and Y, wherein Y represents i) an N-oxide of said five- or six-membered ring, or ii) forms an $OR^a$ linkage wherein $R^a$ is selected from hydrogen and alkyl; and,
$R^9$ and $R^{10}$ are independently selected from hydrogen, alkyl, alkylcarbonyl, alkoxycarbonyl aryl, arylalkyl, and heteroaryl, wherein aryl is optionally substituted with one or more substituent independently selected from halogen, alkyl, or haloalkyl;
—$R^4$ and $R^5$ are taken together to form a fused ring selected from $-C(R^{11})=C(R^{12})C(R^{13})=C(R^{14})-$, $-SC(R^{15})=C(R^{16})-$, $-C(R^{15})=C(R^{16})S-$, and $-CH=C(R^{15})N=CH-$, where
$R^{11}$ and $R^{14}$ are independently selected from hydrogen, halogen, and methyl;
$R^{12}$ is selected from hydrogen, halogen, amino, $(C_1-C_2)$alkyl, methoxy, halomethoxy, $(C_2-C_3)$alkenyl, and $(C_2-C_3)$alkynyl;
$R^{13}$ is selected from hydrogen, halogen, cyano, $(C_1-C_2)$alkyl, hydroxy, methoxy, halomethyl, and $(C_2-C_3)$alkynyl;
and,
$R^{15}$ and $R^{16}$ are independently selected from hydrogen, halogen, cyano, amino, $(C_1-C_2)$alkyl, $(C_2-C_3)$alkenyl, $(C_2-C_3)$alkynyl halomethyl, hydroxy, methoxy, and halomethoxy;
—X is selected from $-CHR^{17}-$, $-CH_2CHR^{17}-$, $-C_3H_6-$, $-C_4H_8-$, $-O-$, $-OCH_2-$, $-OC_2H_4-$, $-OC_3H_6-$, $-CH_2O-$, $-CH_2OCH_2-$, $-CH_2OC_2H_4-$, $-S-$, $-SCH_2-$, $-CH_2S-$, $-CH_2S(O)-$, $-CH_2S(O)_2-$, $-N(R^{17})CH_2-$; and $-CH_2N(R^{17})-$;

where
$R^{17}$ is selected from hydrogen and alkyl; and
agriculturally-acceptable salts thereof;
with the proviso that when R and $R^1$ are hydrogen; $R^2$ and $R^3$ taken together is $=CHN=C(R^7)N(R^8)-$, where $R^7$ and $R^8$ are hydrogen; $R^4$ and $R^5$ taken together is $-C(R^{11})=C(R^{12})C(R^{13})=C(R^{14})-$; and X is $-CHR^{17}$, where $R^{17}$ is hydrogen; then at least one of $R^{11}$, $R^{12}$, $R^{13}$, or $R^{14}$ is other than hydrogen; and,
with the further proviso that when R and $R^1$ are hydrogen; $R^2$ and $R^3$ taken together is $=NCH(R^6)CH(R^7)N(R^8)-$; where $R^6$, $R^7$, and $R^8$ are hydrogen; $R^4$ and $R^5$ taken together is $-C(R^{11})=C(R^{12})C(R^{13})=C(R^{14})-$, and X is $-CHR^{17}$, where $R^{17}$ is hydrogen; then i) when $R^{11}$, $R^{13}$ and $R^{14}$ are hydrogen, then $R^{12}$ is other than methyl; ii) when $R^{11}$ is hydrogen, $R^{13}$ is methyl, and $R^{14}$ is bromo, then $R^{12}$ is other than hydrogen; iii) when $R^{11}$ and $R^{14}$ are hydrogen, and $R^{12}$ is methoxy, then $R^{13}$ is other than methoxy, and iv) when X is $-CH_2CHR^{17}-$, or $OCH_2-$; $R^{17}$ is hydrogen; $R^{11}$ and $R^{14}$ are hydrogen, $R^{12}$ is methoxy, and $R^{13}$ is methyl; then $R^8$ is other than —$S(O)_nR^9$, where n is 2, and $R^9$ is methyl.

Excluding those compositions of compounds set forth in the proviso above, preferred insecticidal compositions of compounds of formula I are those wherein $R^2$ and $R^3$ taken together is =$NCH(R^6)CH(R^7)N(R^8)$—, =$NC(R^6)$=$C(R^7)N(R^8)$—, or =$CHN$=$C(R^7)N(R^8)$—, and tautomers thereof, where $R^8$ is selected from hydrogen, cyano, —$S(O)_nN(R^9)(R^{10})$, and —$P(O)(OR^9)(OR^{10})$, where n is 2, and $R^9$ and $R^{10}$ are independently selected from hydrogen and alkyl; $R^4$ and $R^5$ are taken together to form a fused ring, where $R^4$ and $R^5$ together is —$C(R^{11})$=$C(R^{12})C(R^{13})$=$C(R^{14})$, where $R^{11}$ is hydrogen, $R^{12}$ is selected from halogen and methoxy, and $R^{13}$ is selected from halogen and $(C_1-C_2)$alkyl; and, X is selected from —$CHR^{17}$—, —$CH_2CHR^{17}$—, —$OCH_2$—, and —$SCH_2$—. Particularly preferred insecticidal compositions of compounds are those wherein $R^9$ and $R^{10}$ are each methyl; $R^{12}$ is selected from chlorine and methoxy; $R^{13}$ is selected from chlorine and methyl; and, $R^{14}$ is selected from hydrogen, chlorine and methyl; and X is selected from —$CH_2CHR^{17}$— and —$OCH_2$—, where $R^{17}$ is hydrogen.

One skilled in the art will of course recognize that the formulation and mode of application of a toxicant may affect the activity of the material in a given application. Thus, for agricultural use the present insecticidal compounds may be formulated as a granular of relatively large particle size (for example, 5/16 or 4/8 US Mesh), as water-soluble or water-dispersible granules, as powdery dusts, as wettable powders, as emulsifiable concentrates, as aqueous emulsions, as solutions, or as any of other known types of agriculturally-useful formulations, depending on the desired mode of application. It is to be understood that the amounts specified in this specification are intended to be approximate only, as if the word "about" were placed in front of the amounts specified.

These insecticidal compositions may be applied either as water-diluted sprays, or dusts, or granules to the areas in which suppression of insects is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the insecticidal compound and 99.0 parts of talc.

Wettable powders, also useful formulations for insecticides, are in the form of finely divided particles that disperse readily in water or other dispersant. The wettable powder is ultimately applied to the locus where insect control is needed either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.0 parts of the insecticidal compound, 17.9 parts of Palmetto clay, and 1.0 part of sodium lignosulfonate and 0.3 part of sulfonated aliphatic polyester as wetting agents. Additional wetting agent and/or oil will frequently be added to a tank mix for to facilitate dispersion on the foliage of the plant.

Other useful formulations for insecticidal applications are emulsifiable concentrates (ECs) which are homogeneous liquid compositions dispersible in water or other dispersant, and may consist entirely of the insecticidal compound and a liquid or solid emulsifying agent, or may also contain a liquid carrier, such as xylene, heavy aromatic naphthas, isphorone, or other non-volatile organic solvents. For insecticidal application these concentrates are dispersed in water or other liquid carrier and normally applied as a spray to the area to be treated. The percentage by weight of the essential active ingredient may vary according to the manner in which the composition is to be applied, but in general comprises 0.5 to 95% of active ingredient by weight of the insecticidal composition.

Flowable formulations are similar to ECs, except that the active ingredient is suspended in a liquid carrier, generally water. Flowables, like ECs, may include a small amount of a surfactant, and will typically contain active ingredients in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 15% by weight of the composition.

Other useful formulations include suspensions of the active ingredient in a relatively non-volatile solvent such as water, corn oil, kerosene, propylene glycol, or other suitable solvents.

Still other useful formulations for insecticidal applications include simple solutions of the active ingredient in a solvent in which it is completely soluble at the desired concentration, such as acetone, alkylated naphthalenes, xylene, or other organic solvents. Granular formulations, wherein the toxicant is carried on relative coarse particles, are of particular utility for aerial distribution or for penetration of cover crop canopy. Pressurized sprays, typically aerosols wherein the active ingredient is dispersed in finely divided form as a result of vaporization of a low-boiling dispersant solvent carrier may also be used. Water-soluble or water-dispersible granules are free flowing, non-dusty, and readily water-soluble or water-miscible. In use by the farmer on the field, the granular formulations, emulsifiable concentrates, flowable concentrates, aqueous emulsions, solutions, etc., may be diluted with water to give a concentration of active ingredient in the range of say 0.1% or 0.2% to 1.5% or 2%.

The active insecticidal compounds of this invention may be formulated and/or applied with one or more second compounds. Second compounds include, but are not limited to, other pesticides, plant growth regulators, fertilizers, soil conditioners, or other agricultural chemicals. In applying an active compound of this invention, whether formulated alone or with other agricultural chemicals, an effective amount and concentration of the active compound of course employed; the amount may vary in the range of, e.g. about 0.01 to about 3 kg/ha, preferably about 0.03 to about 1 kg/ha. For field use, where there are losses of insecticide, higher application rates (e.g., four times the rates mentioned above) may be employed.

When the active insecticidal compounds of the present invention are used in combination with one or more of second compounds, e.g., with other pesticides such as herbicides, the herbicides include, without limitation, for example: N-(phosphonomethyl)glycine ("glyphosate"); aryloxyalkanoic acids such as (2,4-dichlorophenoxy)acetic acid ("2,4-D"), (4-chloro-2-methylphenoxy)acetic acid ("MCPA"), (+/−)-2-(4chloro-2-methylphenoxy)propanoic acid ("MCPP"); ureas such as N,N-dimethyl-N'-[4-(1-methylethyl)phenyl]urea ("isoproturon"); imidazolinones such as 2-[4,5-dihydro-4-methyl-4-(1-methylethyl)-5-oxo-1H-imidazol-2-yl]-3-pyridinecarboxylic acid ("imazapyr"), a reaction product comprising (+/−)-2-[4,5-dihydro-4-methyl-4-(1-methylethyl)-5-oxo-1H-imidazol-2-yl]-4-methylbenzoic acid and (+/−)$_2$-[4,5-dihydro-4-methyl-4-(1-methylethyl)-5-oxo-1H-imidazol-2-yl]-5-methylbenzoic acid ("imazamethabenz"), (+/−)-2-[4,5-dihydro-4-methyl-4-(1-methylethyl)-5-oxo-1H-imidazol-2-yl]-5-ethyl-3-pyridinecarboxylic acid ("imazethapyr"), and (+/−)-2-[4,5-dihydro-4-methyl-4-(1-methylethyl)-5-oxo-1H-imidazol-2-yl]-3-quinolinecarboxylic acid ("imazaquin"); diphenyl ethers such as 5-[2-chloro-4-(trifluoromethyl)phenoxy]-2-nitrobenzoic acid ("acifluorfen"), methyl 5-(2,4-dichlorophenoxy)-2-nitrobenzoate ("bifenox"), and 5-[2-chloro-4-(trifluoromethyl)phenoxy]-N-(methylsulfonyl)-2-nitrobenzamide ("fomasafen"); hydroxybenzonitriles such as 4-hydroxy-3,5-diiodobenzonitrile ("ioxynil") and 3,5-dibromo-4-hydroxybenzonitrile ("bromoxynil"); sulfonylureas such as 2-[[[[(4chloro-6-methoxy-2-pyrimidinyl)amino]carbonyl]amino]sulfonyl]benzoic acid ("chlorimuron"), 2-chloro-N-[[(4-methoxy-6-methyl-1,3,5-triazin-2-yl)amino]carbonyl]benzenesulfonamide (achlorsulfuron"), 2-[[[[[(4,6-dimethoxy-2-pyrimidinyl)amino]carbonyl]amino]sulfonyl]methyl]benzoic acid ("bensulfuron"), 2-[[[[(4,6-dimethoxy-2-pyrimidinyl)amino]carbonyl]amino]sulfonyl]-1-methyl-1H-pyrazol-4-carboxylic acid ("pyrazosulfuron"), 3-[[[[(4-methoxy-6-methyl-1,3,5-triazin-2-yl)amino]carbonyl]amino]sulfonyl]-2-thiophenecarboxylic acid ("thifensulfuron"), and 2-(2-chloroethoxy)-N[[(4-methoxy-6-methyl-1,3,5-triazin-2-yl)amino]carbonyl] benzenesulfonamide ("triasulfuron"); 2-(4-aryloxyphenoxy) alkanoic acids such as (+/−)-2[4-[(6-chloro-2-benzoxazolyl) oxy]phenoxy]propanoic acid (fenoxaprop"), (+/−)-2-[4[[5-(trifluoromethyl)-2-pyridinyl]oxy]phenoxy]propanoic acid ("fluazifop"), (+/−)-2-[4-(6chloro-2-quinoxalinyl)oxy]phenoxy]propanoic acid ("quizalofop"), and (+/−)-2-[(2,4-dichlorophenoxy)phenoxy]propanoic acid ("diclofop"); benzothiadiazinones such as 3-(1-methylethyl)-1H-1,2,3-benzothiadiazin-4(3H)-one-2,2-dioxide ("bentazone"); 2-chloroacetanilides such as N-(butoxymethyl)-2-chloro-N-(2,6-diethylphenyl)acetamide ("butachlor"), 2-chloro-N-(2-ethyl-6-methylphenyl)-N-(2-methoxy-1-methylethyl)acetamide ("metolachlor"), 2-chloro-N-(ethoxymethyl)-N-(2-ethyl-6-methylphenyl)acetamide ("acetochlor"), and (RS)-2-chloro-N-(2,4-dimethyl-3-thienyl)-N-(2-methoxy-1-methylethyl)acetamide ("dimethenamide"); arenecarboxylic acids such as 3,6-dichloro-2-methoxybenzoic acid ("dicamba"); pyridyloxyacetic acids such as [(4-amino-3,5-dichloro-6-fluoro-2-pyridinyl)oxy]acetic acid ("fluoroxypyr"), and other herbicides.

When the active insecticidal compounds of the present invention are used in combination with one or more of second compounds, e.g., with other pesticides such as other insecticides, the other insecticides include, for example: organophosphate insecticides, such as chlorpyrifos, diazinon, dimethoate, malathion, parathion-methyl, and terbufos; pyrethroid insecticides, such as fenvalerate, deltamethrin, fenpropathrin, cyfluthrin, flucythrinate, alpha-cypermethrin, biphenthrin, resolved cyhalothrin, etofenprox, esfenvalerate, tralomehtrin, tefluthrin, cycloprothrin, betacyfluthrin, and acrinathrin; carbamate insecticides, such as aldecarb, carbaryl, carbofuran, and methomyl; organochlorine insecticides, such as endosulfan, endrin, heptachlor, and lindane; benzoylurea insecticides, such as diflubenuron, triflumuron, teflubenzuron, chlorfluazuron, flucycloxuron, hexaflumuron, flufenoxuron, and lufenuron; and other insecticides, such as amitraz, clofentezine, fenpyroximate, hexythiazox, spinosad and imidacloprid.

When the active insecticidal compounds of the present invention are used in combination with one or more of second compounds, e.g., with other pesticides such as fungicides, the fungicides include, for example: benzimidazole fungicides, such as benomyl, carbendazim, thiabendazole, and thiophanate-methyl; 1,2,4-triazole fungicides, such as epoxyconazole, cyproconazole, flusilazole, flutriafol, propiconazole, tebuconazole, triadimefon, and triadimenol; substituted anilide fungicides, such as metalaxyl, oxadixyl, procymidone, and vinclozolin; organophosphorus fungicides, such as fosetyl, iprobenfos, pyrazophos, edifenphos, and tolclofos-methyl; morpholine fungicides, such as fenpropimorph, tridemorph, and dodemorph; other systemic fungicides, such as fenarimol, imazalil, prochloraz, tricyclazole, and triforine; dithiocarbamate fungicides, such as mancozeb, maneb, propineb, zineb, and ziram; non-systemic fungicides, such as chlorothalonil, dichlofluanid, dithianon, and iprodione, captan, dinocap, dodine, fluazinam, gluazatine, PCNB, pencycuron, quintozene, tricylamide, and validamycin; inorganic fungicides, such as copper and sulphur products, and other fungicides.

When the active insecticidal compounds of the present invention are used in combination with one or more of second compounds, e.g., with other pesticides such as nematicides, the nematicides include, for example: carbofuran, carbosulfan, turbufos, aldecarb, ethoprop, fenamphos, oxamyl, isazofos, cadusafos, and other nematicides.

When the active insecticidal compounds of the present invention are used in combination with one or more of second compounds, e.g., with other materials such as plant growth regulators, the plant growth regulators include, for example: maleic hydrazide, chlormequat, ethephon, gibberellin, mepiquat, thidiazon, inabenfide, triaphenthenol, paclobutrazol, unaconazol, DCPA, prohexadione, trinexapac-ethyl, and other plant growth regulators.

Soil conditioners are materials which, when added to the soil, promote a variety of benefits for the efficacious growth of plants. Soil conditioners are used to reduce soil compaction, promote and increase effectiveness of drainage, improve soil permeability, promote optimum plant nutrient content in the soil, and promote better pesticide and fertilizer incorporation. When the active insecticidal compounds of the present invention are used in combination with one or more of second compounds, e.g., with other materials such as soil conditioners, the soil conditioners include organic matter, such as humus, which promotes retention of cation plant nutrients in the soil; mixtures of cation nutrients, such as calcium, magnesium, potash, sodium, and hydrogen complexes; or microorganism compositions which promote conditions in the soil favorable to plant growth. Such microorganism compositions include, for example, *bacillus, pseudomonas, azotobacter, azospirillum, rhizobium*, and soil-borne *cyanobacteria*.

Fertilizers are plant food supplements, which commonly contain nitrogen, phosphorus, and potassium. When the active insecticidal compounds of the present invention are used in combination with one or more of second compounds, e.g., with other materials such as fertilizers, the fertilizers include nitrogen fertilizers, such as ammonium sulfate, ammonium nitrate, and bone meal; phosphate fertilizers, such as superphosphate, triple superphosphate, ammonium sulfate, and diammonium sulfate; and potassium fertilizers, such as muriate of potash, potassium sulfate, and potassium nitrate, and other fertilizers.

The following examples further illustrate the present invention, but, of course, should not be construed as in any way limiting its scope. The examples are organized to present protocols for the synthesis of the heterocyclic derivatives of the present invention, set forth a list of such synthesized species, and set forth certain biological data indicating the efficacy of such compounds.

EXAMPLE 1

Synthesis of 1-(2-Imidazolin-2-Yl)-6-Methoxy-5-Methylinidane (Compound 6)

Step A Synthesis of (4-Methoxy-3-methylphenyl)formaldehyde as an Intermediate

A stirred solution of 180 mL (1.6 Molar in hexane: 0.29 mole) of n-butyllithium in 250 mL of THF was cooled to below −60° C., and a solution of 50 grams (0.26 mole) of 5-bromo-2-methoxytoluene (commercially available) was added at a rate to maintain the reaction mixture temperature below −55° C. Upon completion of addition, the reaction mixture was cooled to about −60° C. to −70° C. where it stirred for 70 minutes. After this time, 80 mL (0.99 mole) of DMF was added to the reaction mixture at a rate to maintain the reaction mixture temperature below −50° C. Upon completion of addition, the reaction mixture was poured into an aqueous dilute sodium chloride solution, and then it was extracted with two portions of diethyl ether. The combined extracts were washed with one portion of an aqueous dilute sodium chloride solution, with one portion of an aqueous saturated sodium chloride solution, and then dried with sodium sulfate. The mixture was filtered and the filtrate was concentrated under reduced pressure, yielding 35.7 grams of a residual oil. The oil was purified by column chromatography on silica gel using mixtures of hexane and ethyl acetate as eluant. The appropriate fractions of eluate were combined and concentrated under reduced pressure, yielding 23.2 grams of the subject compound. The NMR spectrum was consistent with the proposed structure.

Step B Synthesis of 3-(4-Methoxy-3-methylphenyl)propanoic Acid (i) as an Intermediate Formic acid, 40.3 grams (0.88 mole), was stirred and cooled to below 5° C., to which was added 36.9 grams (0.37 mole) of triethylamine at a rate to maintain the reaction mixture temperature below 20° C. Upon completion of addition, 22.0 grams (0.15 mole) of (4-methoxy-3-methylphenyl) formaldehyde was added to the reaction mixture, followed by 22.2 grams (0.15 mole) of 2,2-dimethyl-1,3-dioxane-4,6-dione. Upon completion of addition, the reaction mixture was warmed to 60° C. where it stirred for about 15 minutes. The source of heat was removed, during a period when an exothermic reaction with evolution of gas took place within the reaction vessel. The heat source was returned once the exothermic reaction subsided, and heating of the reaction mixture was resumed for about two hours at 75° C. to 95° C. After this time the reaction mixture was cooled in an ice and water bath, and 200 mL of water, followed by 100 mL of aqueous 4N hydrochloric acid were added. The mixture was then extracted with two portions of diethyl ether. The combined extracts were washed with two portions of an aqueous dilute sodium chloride solution, with one portion of an aqueous saturated sodium chloride solution, and then dried with sodium sulfate. The mixture was filtered and the filtrate was concentrated under reduced pressure, yielding a residual solid. The solid was dissolved in an aqueous solution of 1N potassium carbonate and washed with two portions of diethyl ether. The aqueous layer was acidified with concentrated hydrochloric acid, and then it was extracted with two portions of diethyl ether. The combined ether extracts were washed with one portion of an aqueous dilute sodium chloride solution, and then dried with sodium sulfate. The mixture was filtered and concentrated under reduced pressure, yielding 26.3 grams of the subject compound. The NMR spectrum was consistent with the proposed structure.

Step C Synthesis of 6-Methoxy-5-methylindan-1-one (ii) as an Intermediate

Under a dry nitrogen atmosphere, a stirred solution of 5.0 grams (0.029 mole) of 3-(4-methoxy-3-methylphenyl)propanoic acid (i) in 100 mL of Eatons Reagent was heated to about 39° C., at which time an exothermic reaction took place, which raised the reaction mixture temperature to about 49° C. The heat source was removed, and the reaction mixture temperature was allowed to return to 35° C. The heat source was replaced, and the reaction mixture was again warmed to about 39° C. where it stirred for eight hours. After this time the reaction mixture was poured into ice and water, and the mixture was extracted with two portions of methylene chloride. The combined extracts were washed with three portions of an aqueous saturated sodium bicarbonate solution. The organic layer was dried with sodium sulfate and filtered. The filtrate was concentrated under reduced pressure to residue. The residue was purified by column chromatography on silica gel using mixtures of petroleum ether and methylene chloride, then pure methylene chloride, as eluants. The appropriate fractions of eluate were combined and concentrated under reduced pressure, yielding the subject compound. The NMR spectrum was consistent with the proposed structure. This reaction was repeated a second time, yielding a total for the two reactions of 10.7 grams of subject compound.

Step D Synthesis of 5-Methoxy-6-methylinden-3-carbonitrile (iii) as an Intermediate A solution of 10.7 grams (0.061 mole) of 6-methoxy-5-methylindan-1-one (ii), 29.7 grams (0.182 mole) of diethyl cyanophosphonate, and 6.1 grams (0.182 mole) of lithium cyanide in 250 mL of anhydrous THF was stirred at ambient temperature for five hours. GC analysis of the reaction mixture indicated that the reaction was not complete. The reaction mixture was warmed to 45° C., where it was stirred for about 16 hours. After this time, an aliquot of the reaction mixture was placed water and the mixture was extracted with ethyl acetate. GC analysis of the extract indicated that the reaction was about 10% complete. An additional 0.182 mole each of diethyl cyanophosphonate and lithium cyanide were added to the reaction mixture, and heating at 45° C. was continued for about an additional eight hours. After this time, the reaction mixture was poured into about 300 mL of an aqueous solution saturated with sodium chloride, and then it was extracted with two 300 mL portions of ethyl acetate. The combined extracts were then washed with three portions of an aqueous solution saturated with sodium chloride and dried with sodium sulfate. The mixture was filtered and the filtrate was concentrated under reduced pressure to a residue. The residue was dissolved in toluene and again concentrated under reduced pressure to a residue. The residue was taken up in 500 mL of toluene and 20.7 grams (0.182 mole) of boron trifluoride diethyl etherate was added. Upon completion of addition, the reaction mixture was stirred at ambient temperature for about six hours. The reaction mixture was treated as set forth above, yielding a residue. The residue was purified by column chromatography on silica gel using mixtures of hexane and diethyl ether as an eluant. The appropriate fractions of eluate were combined and concentrated under reduced pressure, yielding 2.8 grams of subject compound. The NMR spectrum was consistent with the proposed structure.

Step E Synthesis of 6-Methoxy-5-methylindanecarbonitrile (iv) as an Intermediate Under a nitrogen atmosphere, 0.1 gram (catalyst) of 10% palladium on carbon and 0.05 gram (catalyst) of 5% platinum on carbon were placed in a 250 mL Parr hydrogenation bottle, followed by a solution of 2.5 grams (0.014 mole) of 5-methoxy-6-methylinden-3-carbonitrile (iii) in 100 mL of ethyl acetate. The mixture was hydrogenated in a Parr hydrogenation apparatus for about 45 minutes, during which time the theoretical amount of hydrogen was taken up by the reaction. The reaction mixture was then washed through a pad of diatomaceous earth with methylene chloride. The methylene chloride wash was concentrated under reduced pressure, yielding 2.4 grams of subject compound. The NMR spectrum was consistent with the proposed structure.

Step F Synthesis of The Ethylenediamine Salt of p-Toluenesulfonic Acid as an Intermediate A mixture of 50 grams (0.263 mole) of p-toluenesulfonic acid hydrate and 30 mL of water in 150 grams of ice was stirred, and 22.1 grams (0.368 mole) of ethylenediamine was added in one portion. Upon completion of addition, the reaction mixture was stirred for about 90 minutes. After this time, the reaction mixture was concentrated under reduced pressure to remove a majority of the water, leaving a residue. The residue was taken up in 2-propanol and again concentrated under reduced pressure to a residue. The addition and removal of 2-propanol from the residue was repeated twice more, yielding 61.2 grams of subject compound. The NMR spectrum was consistent with the proposed structure.

Step G Synthesis of Compound 6

A mixture of 2.4 grams (0.013 mole) of 6-methoxy-5-methylindanecarbonitrile (iv) and 11.2 grams (0.045 mole) of the ethylenediamine salt of p-toluenesulfonic acid was stirred and heated to about 140° C.-160° C. where it was maintained for about 4.5 hours. The reaction mixture was then cooled to ambient temperature and dissolved in a mixture of aqueous 5% potassium carbonate and methylene chloride. The organic layer was removed, and the aqueous layer was extracted with two portions of methylene chloride. The combined extracts and organic layer were washed with one portion of aqueous 5% potassium carbonate. The organic layer was dried with sodium sulfate and filtered. The filtrate was concentrated under reduced pressure to a solid residue. The residue was purified by column chromatography on Grade II basic alumina (3% water) using mixtures of methylene chloride and methanol as an eluant. The appropriate fractions of eluate were combined and concentrated under reduced pressure, yielding about 2.1 grams of subject compound. The NMR spectrum was consistent with the proposed structure.

EXAMPLE 2

Synthesis of 1-(2-Imidazolin-2-Yl)-7-Methoxy-6-Methyl-1,2,3,4-Tetrahydronaphthalene (Compound 50)

Step A Synthesis of 4-(4-Methoxy-3-methylphenyl)but-3-yn-1-ol as an Intermediate A stirred solution of 4.6 grams (0.023 mole) of 5-bromo-2-methoxytoluene (commercially available), 3 mL (0.040 mole) of 3-butyn-1-ol, 0.30 gram (0.002 mole) of copper(I) iodide, 14 mL (0.100 mole) of triethylamine, and 0.25 gram (0.0004 mole) of dichlorobis(triphenylphosphine)palladium (II) in 60 mL of DMF was heated at 90° C. for about 18 hours. After this time, the reaction mixture was poured into water and extracted with diethyl ether. The ether extract was dried with sodium sulfate and filtered. The filtrate was concentrated under reduced pressure to a residue. The residue was purified by column chromatography on silica gel using mixtures of hexane and ethyl acetate as an eluant. The appropriate fractions of eluate were combined and concentrated under reduced pressure, yielding 1.5 grams of subject compound. The NMR spectrum was consistent with the proposed structure.

Step B Synthesis of 4-(4-Methoxy-3-methylphenyl)butan-1-ol as an Intermediate

This compound was prepared in a manner analogous to that of Step E of Example 1, by the hydrogenation of 1.4 grams (0.0074 mole) of 4-(4-methoxy-3-methylphenyl)but-3-yn-1-ol in the presence of 0.05 gram (catalyst) of 10% palladium on carbon in 150 mL of methanol. The reaction product was purified by column chromatography on silica gel using mixtures of hexane and ethyl acetate as an eluant. The appropriate fractions of eluate were combined and concentrated under reduced pressure, yielding 0.8 gram of subject compound. The NMR spectrum was consistent with the proposed structure. This reaction was repeated on a larger scale.

Step C Synthesis of 4-(4-Methoxy-3-methylphenyl)butanoic acid (i) as an Intermediate A stirred solution of 1.7 grams (0.009 mole) of 4-(4-methoxy-3-methylphenyl)butan-1-ol in 50 mL of acetone was cooled to 0° C.-4° C., and about 15 to 20 mL (excess) of Jones Reagent was added dropwise. Upon completion of addition, the reaction mixture was stirred at 0° C. for two hours, then it was allowed to warm to ambient temperature, where it stirred for an additional three hours. After this time, the reaction mixture was diluted with isopropanol and filtered. The filter cake was washed with acetone, and the combined filtrate and wash were concentrated under reduced pressure to a residue. The residue was partitioned with methylene chloride and water and the separated organic layer was washed with water. The organic layer was then dried with sodium sulfate and filtered. The filtrate was concentrated under reduced pressure to a residue. The residue was dried under vacuum, yielding 1.1 grams of subject compound. The NMR spectrum was consistent with the proposed structure. The reaction was repeated to obtain an additional amount of subject compound.

Step D Synthesis of 7-Methoxy-6-methyl-2,3,4-trihydronaphthalen-1-one (ii) as an Intermediate This compound was prepared in a manner analogous to that of Step C of Example 1, by the reaction of 0.9 gram (0.0043 mole) of 4-(4-methoxy-3-methylphenyl)butanoic acid (i) in 30 mL of Eaton's Reagent. The reaction product was purified by column chromatography on silica gel using mixtures of hexane and ethyl acetate as an eluant. The appropriate fractions of eluate were combined and concentrated under reduced pressure, yielding 0.6 gram of subject compound. The NMR spectrum was consistent with the proposed structure.

Step E Synthesis of 7-Methoxy-6-methyl-1,2,3,4-tetrahydronaphthalene-carbonitrile (iv) as an Intermediate A stirred solution of 0.6 gram (0.0032 mole) of 7-methoxy-6-methyl-2,3,4-trihydronaphthalen-1-one (ii), 2.2 mL (0.0170 mole) of trimethylsilyl cyanide, and a catalytic amount of aluminum chloride in 20 mL of toluene was warmed to 70° C. where it was maintained for about 18 hours. After this time, the reaction mixture was cooled and taken up in 100 mL of hexane and filtered through diatomaceous earth. The filtrate was concentrated under reduced pressure to a residual oil, which was an intermediate product; namely: 7-methoxy-6-methyl-1-(1,1-dimethyl-1-silaethoxy)-1,2,3,4-tetrahydronaphthalenecarbonitrile (cyano-silyl intermediate). The so-prepared 1-silaethoxy intermediate was then taken up in 100 mL of acetonitrile, along with 2.0 grams (0.013 mole) of sodium iodide, 1.8 mL (0.014 mole) of trimethylsilyl chloride, and 0.1 mL of water, and stirred at ambient temperature for about 72 hours. After this time, the reaction mixture was poured into water and extracted with ethyl acetate. The extract was washed in turn with an aqueous dilute solution of sodium metabisulfite and with water, and then it was dried with sodium sulfate. The mixture was concentrated under reduced pressure to a residue, which was a mixture of subject compound and an intermediate product, namely: 7-methoxy-6-methyl-3,4-dihydronaphthalenecarbonitrile (Intermediate (iii)). In a manner analogous to that of Step E of Example 1, the mixture of subject compound and the 3,4-dihydronaphthalenecarbonitrile intermediate was subjected to hydrogenation using a Parr hydrogenator, in the presence of 0.1 gram (catalyst) of 10% platinum on carbon and 0.1 gram (catalyst) of 10% palladium on carbon in 100 mL of ethyl acetate. Following a 90 minute hydrogenation period, the reaction mixture was filtered through diatomaceous earth. The filter cake was washed with methylene chloride and the combined wash and filtrate were concentrated under reduced pressure to a residue. NMR analyses of the residue indicated that it was still a mixture of subject compound and the 3,4-dihydronaphthalenecarbonitrile intermediate. The hydrogenation of the mixture of subject compound and the 3,4-dihydronaphthalenecarbonitrile intermediate was repeated during a period of seven hours of reaction time. The reaction mixture was then worked-up in the manner set forth above, yielding about 0.25 gram of subject compound. The NMR spectrum was consistent with the proposed structure.

Step F Synthesis of Compound 50

This compound was prepared in a manner analogous to that of Step G of Example 1, by the reaction of 0.1 gram (0.0005 mole) of 7-methoxy-6-methyl-1,2,3,4-tetrahydronaphthalenecarbonitrile (iv) and 1.2 grams (0.0048 mole) of the ethylenediamine salt of p-toluenesulfonic acid (prepared in Step F of Example 1). The reaction product was purified by column chromatography on silica gel using mixtures of methylene chloride and methanol as an eluant. The appropriate fractions of eluate were combined and concentrated under reduced pressure, yielding 0.07 gram of subject compound. The NMR spectrum was consistent with the proposed structure.

EXAMPLE 3

Synthesis of 4-(2-Imidazolin-2-Yl)-7-Methylchromane (Compound 88)

Step A Synthesis of 3-(3-Methylphenoxy)propan-1-ol as an Intermediate

A stirred solution of 25 grams (0.23 mole) of 3-methylphenol and 18.8 grams (0.20 mole) of 3-chloropropan-1-ol in 100 mL of aqueous 10% sodium hydroxide was heated at reflux for about 40 minutes. After this time, the reaction mixture was cooled to ambient temperature and extracted with three 100 mL portions of diethyl ether. The combined extracts were then washed with three 50 mL portions of an aqueous dilute sodium hydroxide solution and dried with sodium sulfate. The mixture was filtered and the filtrate was concentrated under reduced pressure, yielding 29 grams of subject compound. The NMR spectrum was consistent with the proposed structure.

Step B Synthesis of 3-(3-Methylphenoxy)propanoic Acid (i) as an Intermediate

This compound was prepared in a manner analogous to that of Step C of Example 2, by the reaction of 2.0 grams (0.012 mole) of 3-(3-methylphenoxy)propan-1-ol and 10 mL of Jones Reagent in 30 mL of acetone. The yield of subject compound was 1.5 grams. The NMR spectrum was consistent with the proposed structure.

Step C Synthesis of 7-Methylchroman-4-one (ii) as an Intermediate

A stirred solution of 5.0 grams (0.028 mole) of 3-(3-methylphenoxy)propanoic acid (i) and 5.3 grams (0.042 mole) of oxalyl chloride in 100 mL of methylene chloride was cooled to –5° C. and a few drops of DMF was added. Upon completion of addition, the reaction mixture was allowed to warm to ambient temperature where it stirred for about two hours. After this time, the reaction mixture was concentrated under reduced pressure to a residue: which was 3-(3-methylphenoxy)propanoic acid chloride. The acid chloride was stored under a nitrogen atmosphere for about 18 hours, and then it was dissolved in 50 mL of methylene chloride. The stirred solution was cooled to –4° C. and 4.1 grams (0.031 mole) of aluminum chloride was added portionwise while maintaining the reaction mixture temperature at 5° C. or less. Upon completion of addition, the reaction mixture was maintained at 5° C. for about three hours. After this time, the reaction mixture was poured into ice and extracted with three 100 mL portions of methylene chloride. The combined extracts were washed with two 50 mL portions of water and dried with sodium sulfate. The mixture was filtered, and the filtrate was concentrated under reduced pressure to a residue. The residue was purified by column chromatography on silica gel using mixtures of ethyl acetate and hexane as an eluant. The appropriate fractions of eluate were combined and concentrated under reduced pressure, yielding 3.5 grams of subject compound. The NMR spectrum was consistent with the proposed structure.

Step D Synthesis of 7-Methylchromane-4-carbonitrile (iv) as an Intermediate

This compound was prepared in a manner analogous to that of Step E of Example 2, by 1) the reaction of 1.0 gram (0.006 mole) of 7-methylchroman-4-one (ii) with 1.8 gram (0.018 mole) of trimethylsilyl cyanide, in the presence of 0.2 gram (catalyst) of aluminum chloride in 30 mL of toluene, affording an intermediate product, namely: 7-methyl-4-(1,1-dimethyl-1-silaethoxy)chromane-4-carbonitrile (cyano-silyl intermediate), then 2) the reaction of the 1-silaethoxy intermediate with 3 mL (0.024 mole) of trimethylsilyl chloride, 3.6 grams (0.024 mole) of sodium iodide, and 0.2 mL of water in 30 mL of acetonitirile, yielding 0.8 gram of subject compound. Contrary to Step E of Example 2, the hydrogenation step was not necessary to obtain the subject compound. The NMR spectrum was consistent with the proposed structure.

Step E Synthesis of Compound 88

This compound was prepared in a manner analogous to that of Step G of Example 1, by the reaction of 0.6 gram (0.003 mole) of 7-methylchromane-4-carbonitrile (iv) and 2 grams (0.008 mole) of the ethylenediamine salt of p-toluenesulfonic acid (prepared in Step F of Example 1). The reaction product was purified by column chromatography on Grade II basic alumina (3% water) using mixtures of methylene chloride and methanol as an eluant. The appropriate fractions of eluate were combined and concentrated under reduced pressure, yielding 0.25 gram of subject compound. The NMR spectrum was consistent with the proposed structure.

EXAMPLE 4

Synthesis of 1-(Imidazol-5-Yl)-6-Methoxy-5-Methylindane (Compound 257)

Step A Synthesis of a Mixture of 2,4,5-triiodoimidazole and 2,5-diiodoimidazole (v) as an Intermediate A stirred solution of 15.0 grams (0.220 mole) of imidazole (commercially available) in 10 mL of aqueous 2N sodium hydroxide was cooled to about 10° C. and an additional 540 mL of aqueous 2N sodium hydroxide was added. Solid iodine, 168 grams (0.661 mole), was taken up in 500 mL of methylene chloride, in which some of the iodine did not dissolve. An additional 500 mL of methylene chloride was added to the iodine mixture, which also failed to dissolve all of the iodine. The solution of dissolved iodine was then added dropwise to the aqueous solution of imidazole during a one hour period while maintaining the reaction mixture temperature about 10° C. Upon completion of addition, the undissolved iodine was then added portion wise to the imidazole solution during an additional one hour period. Upon completion of addition, the reaction mixture was allowed to warm to ambient temperature, where it stirred for about 18 hours. The aqueous layer was separated from the reaction mixture and was treated with solid sodium bisulfate to decompose any unreacted iodine in it. The pH of the aqueous layer was then adjusted to about 5 with concentrated hydrochloric acid, and the mixture was extracted with three portions of ethyl acetate. The combined extracts were dried with sodium sulfate and filtered. The filtrate was concentrated under reduced pressure to a residue. Thin layer chromatographic analysis of the residue indicated that it was a mixture of 2,4,5-triiodoimidazole and 2,5-diiodoimidazole. The residue was triturated with a small amount of ethyl acetate and filtered to collect a solid. The filtrate was concentrated under reduced pressure to a residue, yielding when dried about 17.9 grams of 2,4,5-triiodoimidazole. The solid collected by filtration was dried, yielding about 41.7 grams of 2,5-diiodoimidazole. The NMR spectra of 2,4,5-iodo and the 2,5-iodo derivatives were consistent with the proposed structure.

Step B Synthesis of 5-iodoimidazole (vi) as an Intermediate

A solution of a mixture of 17.9 grams (0.040 mole) of 2,4,5-triiodoimidazole and 41.7 grams (0.130 mole) of 2,5-diiodoimidazole (v) and 500 mL of ethanol in 1500 mL of water was stirred, and 75 grams (0.595 mole) of sodium sulfite was added portion wise. Upon completion of addition, the reaction mixture was warmed to reflux, where it stirred for about 18 hours. After this time, the reaction mixture was cooled to ambient temperature and concentrated under reduced pressure to remove ethanol. The aqueous concentrate was extracted with two 700 mL portions of ethyl acetate and two 250 mL portions of n-butanol. The combined extracts were dried with sodium sulfate and filtered. The filtrate was concentrated under reduced pressure to a residue. The residue was slurried in water, and the resultant solid was collected by filtration, yielding when dried about 13.2 grams of subject compound. The NMR spectrum was consistent with the proposed structure.

Step C Synthesis of 1-(triphenylmethyl)-4-iodoimidazole (vii) as an Intermediate DMF, 100 mL, was stirred, and 13.2 grams (0.068 mole) of 5-iodoimidazole (vi) was added, followed by 18.9 grams (0.068 mole) of triphenylmethyl chloride, and 3.3 grams (0.033 mole) of triethylamine. Upon completion of addition, the reaction mixture was stirred at ambient temperature for 18 hours. After this time, the reaction mixture was poured into crushed ice where it stirred until the ice melted. The resultant solid was then collected by filtration and triturated with diethyl ether. A solid was collected by filtration and washed with diethyl ether, yielding the subject compound. The diethyl ether filtrate was concentrated under reduced pressure to a residue, and re-triturated with diethyl ether, yielding additional subject compound. The total yield of subject compound was about 5.0 grams. The NMR spectrum was consistent with the proposed structure.

Step D Synthesis of 3-(Imidazol-5-yl)-5-methoxy-6-methylindene (viii) as an Intermediate A stirred solution of 5.0 grams (0.012 mole) of 1-(triphenylmethyl)-4-iodoimidazole (vii) in about 200 mL of anhydrous methylene chloride was cooled to about 21° C., and 3.84 mL (3.0M in diethyl ether: 0.012 mole) of ethylmagnesium bromide was added. Upon completion of addition, the reaction mixture was stirred for about one hour at 23° C., and then a solution of 2.0 grams (0.012 mole) of 6-methoxy-5-methylindan-1-one (ii) (prepared in a manner analogous to Step D of Example 1) in 50 mL of methylene chloride was added in one portion. Upon completion of addition, the reaction mixture was stirred at ambient temperature for about 18 hours. After this time, the reaction mixture was poured into a separatory funnel containing an aqueous saturated solution of ammonium chloride. The organic layer was separated and the aqueous layer was extracted with two portions of methylene chloride. The combined extracts and organic layer were dried with sodium sulfate and filtered. The filtrate was concentrated under reduced pressure to a residue. The residue was dissolved in methanol and aqueous 4N hydrochloric acid was then added to the solution. Upon completion of addition, the mixture was stirred at ambient temperature for about 18 hours. After this time, the methanol was removed from the mixture under reduced pressure, leaving an aqueous residue. The residue was washed with three portions of diethyl ether, then the pH of the residue was adjusted to about 8-9 by the addition of solid sodium carbonate. The mixture was then extracted with methylene chloride, and the extract was dried with sodium sulfate. The mixture was filtered and the filtrate was concentrated under reduced pressure to a residue. The residue was again treated with aqueous 4N hydrochloric acid, and the mixture was washed with diethyl ether. The pH of the aqueous layer was adjusted to about 8-9 by the addition of solid sodium carbonate. The mixture was then extracted with methylene chloride, and the extract was dried with sodium sulfate. The mixture was filtered and the filtrate was concentrated under reduced pressure, yielding about 0.5 gram of subject compound. The NMR spectrum was consistent with the proposed structure.

Step E Synthesis of Compound 257

This compound was prepared in a manner analogous to that of Step E of Example 1, by the hydrogenation of 0.5 gram (0.0022 mole) of 3-(imidazol-5-yl)-5-methoxy-6-methylindene (viii) in the presence of 0.1 gram (catalyst) of 10% palladium on carbon and 0.1 gram (catalyst) of platinum oxide hydrate in 40 mL of ethanol. The yield of subject compound was 0.42 gram, mp 68-70° C. The NMR spectrum was consistent with the proposed structure.

EXAMPLE 5

Synthesis of 4-(2-Imidazolin-2-Yl)-6-Methoxy-7-Methylchromane (Compound 89)

Step A Synthesis of 3-(4-Methoxy-3-methylphenoxy)propanenitrile as an Intermediate A solution of 7.0 grams (0.050 mole) of 3-methyl-4-methoxyphenol (known compound) in 20 mL of acrylonitrile was stirred, and 0.4 mL of benzyltrimethylammonium hydroxide (Triton® B) was added. Upon completion of addition, the reaction mixture was warmed to reflux where it stirred during a 21 hour period. The reaction mixture was then cooled to ambient temperature and diluted with 100 mL of diethyl ether. The mixture was then first washed with three 50 mL portions of an aqueous solution of 10% potassium hydroxide, then with three 50 mL portions of aqueous 4N hydrochloric acid. The organic layer was dried with sodium sulfate, and the mixture was filtered. The filtrate was concentrated under reduced pressure, yielding 6.0 grams of the subject compound. The NMR spectrum was consistent with the proposed structure.

Step B Synthesis of 3-(4-Methoxy-3-methylphenoxy)propanoic acid (i) as an Intermediate A stirred solution of 4.0 grams (0.048 mole) of 3-(4-methoxy-3-methylphenoxy)propanenitrile in 100 mL of concentrated hydrochloric acid was heated at reflux during a six hour period. The reaction mixture was then allowed to cool to ambient temperature as it stirred during an additional 18 hour period. After this time a solid precipitate was collected by filtration, washed with water, and then it was dissolved in aqueous 10% potassium hydroxide. The resultant solution was filtered, and the filtrate was acidified with concentrated hydrochloric acid. The resultant precipitate was collected by filtration, washed with water, and then it was dissolved in ethyl acetate. The solution was dried with sodium sulfate and the mixture was filtered. The filtrate was concentrated under reduced pressure, yielding 2.4 grams of the subject compound. The NMR spectrum was consistent with the proposed structure.

Step C Synthesis of 6-Methoxy-7-methyl-chroman-4-one (ii) as an Intermediate

This compound was prepared in a manner analogous to that of Step C of Example 3, by the reaction of 0.1 gram (0.00056 mole) of 3-(4-methoxy-3-methylphenoxy)propanoic acid (i), 0.1 gram (0.00084 mole) of oxalyl chloride and a few drops of DMF in 10 mL of methylene chloride at about 5° C., yielding the corresponding propanoic acid chloride. The acid chloride was then treated with 0.08 gram (0.00061 mole) of aluminum chloride in 10 mL of methylene chloride at about 0° C., yielding 0.09 gram of the subject compound. The NMR spectrum was consistent with the proposed structure. The reaction was repeated on a larger scale.

Step D Synthesis of 6-Methoxy-7-methylchromane-4-carbonitrile (iv) as an Intermediate This compound was prepared in a manner analogous to that of Step E of Example 2, by 1) the reaction of 0.9 gram (0.0046 mole) of 6-methoxy-7-methylchroman-4-one (ii) with 1.40 grams (0.0138 mole) of trimethylsilyl cyanide, in the presence of 0.1 gram (catalyst) of aluminum chloride in 30 mL of toluene, affording an intermediate product, namely: 6-methoxy-7-methyl-4-(1,1-dimethyl-1-silaethoxy)chromane-4-carbonitrile (cyano-silyl intermediate), then 2) the reaction of the 1-silaethoxy intermediate with 2.35 mL (0.0184 mole) of trimethylsilyl chloride, 2.8 grams (0.0184 mole) of sodium iodide, and 0.12 mL of water in 30 mL of acetonitirile, yielding 0.6 gram of subject compound. Contrary to Step E of Example 2, the hydrogenation step was not necessary to obtain the subject compound. The NMR spectrum was consistent with the proposed structure.

Step E Synthesis of Compound 89

This compound was prepared in a manner analogous to that of Step G of Example 1, by the reaction of 0.5 gram (0.002 mole) of 7-methyl-6-methoxychromane-4-carbonitrile (iv) and 2 grams (0.008 mole) of the ethylenediamine salt of p-toluenesulfonic acid (prepared in Step F of Example 1). The reaction product was purified by column chromatography on Grade II basic alumina (3% water) using a 99:1 mixture of methylene chloride and methanol, respectively, as an eluant. The appropriate fractions of eluate were combined and concentrated under reduced pressure, yielding 0.30 gram of subject compound. The NMR spectrum was consistent with the proposed structure.

EXAMPLE 6

Synthesis of 4-(2-Imidazolin-2Yl)-7-Methyl-2H,3H, 4H-Benzo[e]Thiin (Compound 141)

Step A Synthesis of Methyl 3-(3-methylphenylthio)propanoate as an Intermediate

Triethylamine, 0.8 gram (0.009 mole), was added to a solution of 1.0 gram (0.008 mole) of 3-methylbenzenethiol and 1.4 grams (0.009 mole) of methyl 3-bromopropanoate in 10 mL of DMF. Upon completion of addition, the reaction caused the reaction mixture temperature to rise to about 30° C. The reaction mixture was then shaken during a one hour period using a mechanical shaker. After this time, GC analysis of the reaction mixture indicated the reaction was complete. NMR analysis of the reaction mixture indicated that the subject compound was obtained.

The reaction was repeated by cooling a solution of 15.7 grams (0.126 mole) of 3-methylbenzenethiol and 23.3 grams (0.139 mole) of methyl 3-bromopropanoate in about 140 mL of DMF in an ice water bath prior to the addition of 14.1 grams (0.139 mole) of triethylamine. Upon completion of addition, the reaction mixture was allowed to warm to ambient temperature where it stirred for an 18 hour period. The reaction mixture was then poured into 200 mL of water, and the mixture was extracted with three 200 mL portions of ethyl acetate. The combined extracts were washed with water, and then with three 50 mL portions of an aqueous solution saturated with sodium chloride. The organic layer was dried with sodium sulfate, and the mixture was filtered. The filtrate was concentrated under reduced pressure to a residue, yielding 23.5 grams of the subject compound. The NMR spectrum was consistent with the proposed structure.

Step B Synthesis of 3-(3-Methylphenylthio)propanoic acid (i) as an Intermediate

A solution of 22.0 grams (0.105 mole) of methyl 3-(3-methylphenylthio)propanoate in 200 mL of methanol was stirred, and 40 mL of aqueous 10% potassium hydroxide was added. Upon completion of addition, the reaction mixture was stirred at ambient temperature during an 18 hour period. GC analysis of the reaction mixture indicated that the reaction was not complete. An additional 30 mL of the aqueous 10% potassium hydroxide was added, and the reaction mixture was stirred for an additional three hours. After this time, 100 mL of water was added to the reaction mixture and the methanol was removed under reduced pressure. The residue was washed with three 50 mL portions of diethyl ether. The cooled residue was then acidified with aqueous 10% hydrochloric acid, and extracted with 100 mL of diethyl ether. The extract was dried with sodium sulfate and filtered. The filtrate was concentrated under reduced pressure to an oily residue. The residue was stirred with hexane and cooled, resulting in a solid material being formed. The solid was collected by filtration and dried, yielding 17.0 grams of the subject compound. The NMR spectrum was consistent with the proposed structure.

Step C Synthesis of 7-Methyl-2H,3H-benzo[e]thiin-4-one (ii) as an Intermediate

This compound was prepared in a manner analogous to that of Step C of Example 3, by the reaction of 15.0 grams (0.077 mole) of 3-(3-methylphenylthio)propanoic acid (i), 14.5 grams (0.116 mole) of oxalyl chloride and a few drops of DMF in 200 mL of methylene chloride at about 5° C., yielding the corresponding propanoic acid chloride. The acid chloride was then treated with 11.3 grams (0.085 mole) of aluminum chloride in 200 mL of methylene chloride at about 0° C. The reaction product was purified by column chromatography on silica gel using mixtures of ethyl acetate and hexane as an eluant. The appropriate fractions of eluate were combined and concentrated under reduced pressure, yielding 7.0 grams of the subject compound. The NMR spectrum was consistent with the proposed structure.

Step D Synthesis of 7-Methyl-2H,3H,4H-benzo[e]thiin-4-carbonitrile (iv) as an Intermediate This compound was prepared in a manner analogous to that of Step E of Example 2, by 1) the reaction of 3.5 grams (0.0196 mole) of 7-methyl-2H,3H-benzo[e]thiin-4-one (ii) with 11.2 grams (0.0588 mole) of trimethylsilyl cyanide, in the presence of 0.3 gram (catalyst) of aluminum chloride in about 100 mL of toluene, affording an intermediate cyanosilyl product, then 2) the reaction of the cyano-silyl product with 8.5 grams (0.0784 mole) of trimethylsilyl chloride, 11.8 grams (0.0784 mole) of sodium iodide, and 0.52 mL of water in 100 mL of acetonitirile, yielding 3.3 grams of the subject compound. Contrary to Step E of Example 2, the hydrogenation step was not necessary to obtain the subject compound. The NMR spectrum was consistent with the proposed structure.

Step E Synthesis of Compound 141

This compound was prepared in a manner analogous to that of Step G of Example 1, by the reaction of 2.0 grams (0.0106 mole) of 7-methyl-2H,3H,4H-benzo[e]thiin-4-carbonitrile (iv) and 6 grams (0.024 mole) of the ethylenediamine salt of p-toluenesulfonic acid (prepared in Step F of Example 1). The reaction product was purified by column chromatography on Grade II alumina (basic-3% water) using a 99:1 mixture of methylene chloride and methanol, respectively, as an eluant. The appropriate fractions of eluate were combined and concentrated under reduced pressure, yielding 1.2 grams of subject compound. The NMR spectrum was consistent with the proposed structure.

EXAMPLE 7

Synthesis of {[4-(6-Methoxy-7-Methylchroman-4-Yl)Imidazolyl]Sulfonyl}Dimethylamine (Compound 278)

Step A Synthesis of {[4-(4-Hydroxy-6-methoxy-7-methyl-chroman-4-yl)imidazolyl]sulfonyl}dimethylamine (viii) as an Intermediate A solution of 4.6 grams (0.016 mole) of [(4-iodoimidazolyl)sulfonyl]dimethylamine (commercially available) in 10 mL of dry methylene chloride was stirred and 5.7 mL (0.018 mole) of ethylmagnesium bromide (3M in diethyl ether) was added. Upon completion of addition, the reaction mixture was stirred during a 2.5 hour period. After this time, 3.0 grams (0.016 mole) of 6-methoxy-7-methylchroman-4-one (ii) (prepared in Step C of Example 5) was added, and the reaction mixture was stirred for an additional 18 hours. After this time, the reaction mixture was poured into 100 mL of an aqueous solution of ammonium chloride and extracted with three 100 mL portions of methylene chloride. The combined extracts were washed with one 50 mL portion of water, and dried with sodium sulfate. The mixture was filtered and the filtrate was concentrated under reduced pressure to a residue. The residue was purified by column chromatography on Grade II basic alumina (3% water) using a 99:1 mixture of methylene chloride and methanol, respectively, as an eluant. The appropriate fractions of eluate were combined and concentrated under reduced pressure, yielding 3.3 grams of the subject compound. The NMR spectrum was consistent with the proposed structure.

Step B Synthesis of {[4-(6-Methoxy-7-methyl(2H-chromen-4-yl)imidazolyl]sulfonyl}dimethylamine (ix) as an Intermediate A stirred solution of 0.1 gram (0.00027 mole) of {[4-(4-hydroxy-6-methoxy-7-methylchroman-4-yl)imidazolyl] sulfonyl}dimethylamine (ix) in 10 mL of methylene chloride was cooled in an ice water bath, and 0.2 mL of trifluoroacetic acid was added. Upon completion of addition, the reaction mixture was allowed to warm to ambient temperature as it stirred during a one hour period. After this time, the reaction mixture was poured into 20 mL of an aqueous solution of sodium bicarbonate. The mixture was extracted with three 30 mL portions of methylene chloride. The combined extracts were dried with sodium sulfate and filtered. The filtrate was concentrated under reduced pressure to a residue. An NMR spectrum of the residue was consistent with the proposed structure. The reaction was repeated on a larger scale, using 1.5 grams (0.0041 mole) of {[4-(4-hydroxy-6-methoxy-7-methylchroman-4-yl)imidazolyl]sulfonyl}dimethylamine (ix); yielding 1.3 grams of the subject compound. The NMR spectrum was consistent with the proposed structure.

Step C Synthesis of Compound 278

A mixture of 0.1 gram (0.0004 mole) of {[4-(6-methoxy-7-methyl(2H-chromen-4-yl)imidazolyl] sulfonyl}dimethylamine (ix), 0.01 gram (catalyst) of 10% palladium on carbon, and 0.005 gram (catalyst) of 5% platinum on carbon in 75 mL of methanol was subjected to hydrogenation conditions during a two hour period using a Parr hydrogenator. After this time, the reaction mixture was passed through a column of silica gel to remove the catalysts. The eluate was concentrated under reduced pressure to a residue. An NMR spectrum of the residue was consistent with the proposed structure. The reaction was repeated on a larger scale, using 1.1 grams (0.0044 mole) of {[4-(6-methoxy-7-methyl(2H-chromen-4-yl)imidazolyl] sulfonyl}dimethylamine. The reaction product was purified by column chromatography on Grade II alumina (basic-3% water) using methylene chloride and a 99.5:0.5 mixture of methylene chloride and methanol, respectively, as eluants. The appropriate fractions of eluate were combined and concentrated under reduced pressure, yielding 0.38 gram of the subject compound, mp 138-139° C. The NMR spectrum was consistent with the proposed structure.

EXAMPLE 8

Synthesis of 1-Imidazol-2-Yl-7-Methoxy-6-Methyl-1,2,3,4-Tetrahdronanaphthaline (Compound 215)

Step A Synthesis of 1-(Imidazolylmethoxy)-3,3-dimethyl-3-silabutane (xi) as an Intermediate A stirred suspension of 1.2 grams of 60% sodium hydride (0.03 mole-in mineral oil) in 25 mL of THF was cooled to 0° C. to 5° C., and a solution of 2.0 grams (0.03 mole) of imidazole in 30 mL of THF was added dropwise. Upon completion of addition, the reaction mixture was stirred at 0° C. for an additional 15 minutes, then a solution of 4.7 grams (0.03 mole) of 2-(trimethylsilyl)ethoxymethyl chloride in 10 mL of THF was added dropwise. Upon completion of addition, the reaction mixture was allowed to warm to ambient temperature as it stirred during an 18 hour period. After this time, the reaction mixture was stirred with 50 mL of water, and the mixture was extracted with ethyl acetate. The extract was washed with an aqueous solution saturated with sodium chloride and was then dried with magnesium sulfate. The mixture was filtered and the filtrate was concentrated under reduced pressure to a residual oil. The residue was distilled under reduced pressure, yielding 3.8 grams of the subject compound; bp 71° C./0.1 torr. The NMR spectrum was consistent with the proposed structure.

Step B Synthesis of 7-Methoxy-6-methyl-3,4-dihydronaphthyl (trifluoromethyl)sulfonate (x) as an Intermediate This compound was prepared in a manner analogous to that set forth by Pal (*Synthesis* 1995, 1485), by the reaction of 4.2 grams (0.022 mole) of 7-methoxy-6-methyl-2,3,4-trihydronaphthalen-1-one (ii), 22 mL (0.022 mole) of lithium hexamethyldisilazane (1M solution), and 7.8 grams (0.022 mole) of N-phenyltrifluoromethanesulfonimide in 30 mL of THF. The yield of the subject compound was 4.1 grams. The NMR spectrum was consistent with the proposed structure.

Step C Synthesis of 1-{[2-(7-Methoxy-6-methyl(3,4-dihydronaphthyl))imidazolyl]methoxy}-3,3-dimethyl-3-silabutane (xii) as an Intermediate A stirred solution of 1.7 grams (0.009 mole) of 1-(imidazolylmethoxy)-3,3-dimethyl-3-silabutane (xi) in 20 mL of THF was cooled to −78° C., and 5.63 mL (0.009 mole) of n-butyllithium (1.6M in hexane) was added. Upon completion of addition, the reaction mixture was stirred at about −70° C. during a one hour period, then 25 mL (0.025 mole) of zinc chloride (1.0M in diethyl ether) was added. The reaction mixture was then stirred at about −78° C. during a 15 minute period, after which time it was allowed to warm to ambient temperature as it stirred during an additional one hour period. Following this, 2.6 grams (0.009 mole) of 7-methoxy-6-methyl-3,4-dihydronaphthyl (trifluoromethyl)sulfonate (x), then 0.05 gram (catalyst) of tetrakis(triphenylphosphine)palladium(0) were added. Upon completion of addition, the reaction mixture was warmed to 60° C. where it stirred during a two hour period. The reaction mixture was then cooled and concentrated under reduced pressure to a residue. The residue was purified by column chromatography on silica gel using a mixture of 97:3 methylene chloride and methanol, respectively, as an eluant. The appropriate fractions of eluate were combined and concentrated under reduced pressure, yielding 3.4 grams of the subject compound. The NMR spectrum was consistent with the proposed structure.

Step D Synthesis of 4-Imidazol-2-yl-6-methoxy-7-methyl-1,2-dihydronaphthalene (xiii) as an Intermediate A stirred solution of 3.0 grams (0.0081 mole) of 1-{[2-(7-methoxy-6-methyl(3,4-dihydronaphthyl))imidazolyl]methoxy}-3,3-dimethyl-3-silabutane (xii), 5 mL of aqueous 3N hydrochloric acid, and 25 mL (0.025 mole) of tetrabutylammonium fluoride (1.0M in THF) was warmed to 50° C. where it stirred for about two hours. After this time, analysis of the reaction mixture using thin layer chromatography indicated that the reaction had not gone to completion. The reaction mixture was concentrated under reduced pressure to a residue and 15 mL of concentrated hydrochloric acid was added. Upon completion of addition, the reaction mixture was stirred at ambient temperature during an 18 hour period. After this time, the reaction mixture was poured into a mixture of aqueous 50% sodium hydroxide and ice. The mixture was stirred until the ice melted, and a solid was collected by filtration. The solid was washed with ethyl acetate and dried, yielding 1.2 grams of the subject compound, mp 197-229° C. The NMR spectrum was consistent with the proposed structure.

Step E Synthesis of Compound 215

This compound was prepared in a manner analogous to that of Step C of Example 7, by the hydrogenation of 0.7 gram (0.003 mole) of 4-imidazol-2-yl-6-methoxy-7-methyl-1,2-dihydronaphthalene (xiii) using a Parr hydrogenator, in the presence of 0.1 gram (catalyst) of platinum oxide and 0.1 gram (catalyst) of 10% palladium on carbon in 50 mL of ethanol. The yield of the subject compound was 0.34 gram, mp 168-169° C. The NMR spectrum was consistent with the proposed structure.

EXAMPLE 9

Synthesis of 2-(7-Methoxy-6-Methyl-1,2,3,4-Tetrahydronaphthyl)-2-Imidazolinecarbonitrile (Compound 201)

In a 9.5 dram screw cap vial was placed 0.20 gram (0.0008 mole) of Compound 50 (prepared as set forth in Example 2), 0.11 gram (0.0008 mole) of N,N-diisopropylethylamine, and 25 mL of methylene chloride; followed by 2.4 mL (0.0008 mole) of a stock solution of 1 mL of cyanogen bromide in 30 mL of methylene chloride. The reaction mixture was then gently shaken during an 18 hour period using a mechanical shaker. After this time the reaction mixture was poured into ice water in a separatory funnel, and the mixture was extracted with three portions of methylene chloride. The combined extracts were dried with sodium sulfate and filtered. The filtrate was concentrated under reduced pressure to a residual oil. The residual oil was purified by column chromatography on Grade II alumina (basic-3% water) using methylene chloride as an eluant. The appropriate fractions of eluate were combined and concentrated under reduced pressure, yielding 0.19 gram of Compound 201. The NMR spectrum was consistent with the proposed structure.

EXAMPLE 10

Synthesis of 4{[2-(6-Methoxy-7-Methylchroman-4-Yl)(2-Imidazolinyl)]Sulfonyl}Dimethylamine (Compound 203)

A stirred solution of 0.2 gram (0.00081 mole) of Compound 89 (prepared as set forth in Example 5) and 0.16 gram (0.00081 mole) of N,N-diisopropylethylamine in 10 mL of methylene chloride was cooled in an ice water bath for 10 minutes, then 2.63 mL (0.00081 mole) of a stock solution prepared from 1 mL of N,N-dimethylsulfonyl chloride in 30 mL of methylene chloride was added. Upon completion of addition, the reaction mixture was allowed to warm to ambient temperature as it stirred during an 18 hour period. After this time, the reaction mixture was poured into a separatory funnel, followed by an aqueous solution saturated with ammonium chloride, and then methylene chloride. The mixture was shaken and the organic layer was separated, which was then washed with three portions of an aqueous solution saturated with ammonium chloride. The organic layer was dried with sodium sulfate, and the mixture was filtered. The filtrate was concentrated under reduced pressure to a residue. The residue was then dissolved in methylene chloride and placed on a Grade II basic alumina (3% water) column for purification. Elution was accomplished using methylene chloride. The appropriate fractions of eluate were combined and concentrated under reduced pressure, yielding 0.16 gram of Compound 203. The NMR spectrum was consistent with the proposed structure.

EXAMPLE 11

Synthesis of Dimethoxy[2-(6-Methoxy-7-Methyl-chroman-4-Yl)(2-Imidazolinyl)Phosphino-1-One (Compound 204)

This compound was prepared in a manner analogous to that of Example 10, by the reaction of 0.2 gram (0.00081 mole) of Compound 89 (prepared as set forth in Example 5), 2.63 mL (0.00081 mole) of a stock solution prepared from 1 mL of chlorodimethylphosphate in 30 mL of methylene chloride, and 0.16 gram (0.00081 mole) of N,N-diisopropylethylamine in 10 mL of methylene chloride. The crude product was purified by column chromatography on Grade II basic alumina (3% water) using a 99.5:0.5 mixture of methylene chloride and methanol, respectively, as an eluant. The appropriate fractions of eluate were combined and concentrated under reduced pressure, yielding about 0.19 gram of Compound 204. The NMR spectrum was consistent with the proposed structure.

The following table sets forth some additional examples of compounds of the present invention:

TABLE 1

Pesticidal Heterocycles

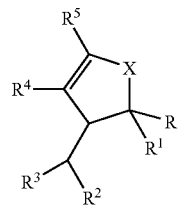

Where
R, $R^1$ and $R^8$ are hydrogen; $R^2$ and $R^3$ taken together is
=NCH($R^6$)CH($R^7$)N($R^8$)—;
and $R^4$ and $R^5$ taken together is —C($R^{11}$)=C($R^{12}$)C($R^{13}$)=C($R^{14}$)—:

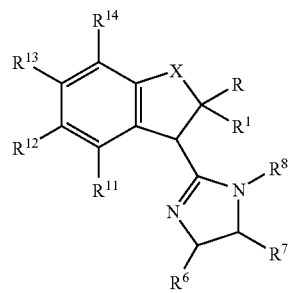

| Cmpd. No. | X | $R^{17}$ | $R^6$ | $R^7$ | $R^{11}$ | $R^{12}$ | $R^{13}$ | $R^{14}$ |
|---|---|---|---|---|---|---|---|---|
| 1 | —CHR$^{17}$— | H | H | H | H | H | CH$_3$ | H |
| 2 HCl Salt | —CHR$^{17}$— | H | H | H | H | H | CH$_3$ | H |
| 3 | —CHR$^{17}$— | H | H | H | H | F | CH$_3$ | H |
| 4 | —CHR$^{17}$— | H | H | H | H | OCH$_3$ | Cl | H |
| 5 | —CHR$^{17}$— | H | H | H | H | OCH$_3$ | I | H |
| 6 | —CHR$^{17}$— | H | H | H | H | OCH$_3$ | CH$_3$ | H |
| 7 | —CHR$^{17}$— | H | H | H | H | OCH$_3$ | CH$_3$ | H |

TABLE 1-continued

Pesticidal Heterocycles

| | | | | | | | | |
|---|---|---|---|---|---|---|---|---|
| 8 HCl Salt | —CHR$^{17}$— | H | H | H | H | H | H | Cl |
| 9 | —CHR$^{17}$— | H | H | H | H | H | Cl | H |
| 10 | —CHR$^{17}$— | H | H | H | H | Cl | H | H |
| 11 HCl Salt | —CHR$^{17}$— | H | H | H | H | Cl | Cl | H |
| 12 | —CHR$^{17}$— | H | H | H | H | H | H | CH$_3$ |
| 13 HCl Salt | —CHR$^{17}$— | H | H | H | H | H | CH$_3$ | H |
| 14 | —CHR$^{17}$— | H | H | H | H | H | CH$_3$ | H |
| 15 HCl Salt | —CHR$^{17}$— | H | H | H | CH$_3$ | H | H | H |
| 16 HCl Salt | —CHR$^{17}$— | H | H | H | CH$_3$ | H | CH$_3$ | H |
| 17 HCl Salt | —CHR$^{17}$— | H | H | H | H | H | F | H |
| 18 HCl Salt | —CHR$^{17}$— | H | H | H | H | H | OH | H |
| 19 | —CHR$^{17}$— | H | H | H | H | OCH$_3$ | Cl | H |
| 20 | —CHR$^{17}$— | H | H | H | H | OCH$_3$ | CH$_3$ | H |
| 21 | —CHR$^{17}$— | H | H | H | H | I | CH$_3$ | H |
| 22 | —CHR$^{17}$— | H | H | H | H | Cl | Cl | H |
| 23 | —CHR$^{17}$— | H | H | H | H | H | CH$_3$ | Cl |
| 24 | —CHR$^{17}$— | H | H | H | H | OCHF$_2$ | CH$_3$ | H |
| 25 | —CHR$^{17}$— | H | H | H | H | OCF$_3$ | CH$_3$ | H |
| 26 | —CHR$^{17}$— | H | H | H | H | NH$_2$ | CH$_3$ | H |
| 27 | —CHR$^{17}$— | H | H | H | H | CH=CH$_2$ | CH$_3$ | H |
| 28 | —CHR$^{17}$— | H | H | H | H | CH=CHCH$_3$ | CH$_3$ | H |
| 29 | —CHR$^{17}$— | H | H | H | H | C≡H | CH$_3$ | H |
| 30 | —CHR$^{17}$— | H | H | H | H | C≡CCH$_3$ | CH$_3$ | H |
| 31 | —CHR$^{17}$— | CH$_3$ | H | H | H | OCH$_3$ | CH$_3$ | H |
| 32 | —CHR$^{17}$— | H | CH$_3$ | H | H | OCH$_3$ | CH$_3$ | H |
| 33 | —CHR$^{17}$— | H | H | CH$_3$ | H | OCH$_3$ | CH$_3$ | H |
| 34 | —CHR$^{17}$— | H | CH$_3$ | CH$_3$ | H | OCH$_3$ | CH$_3$ | H |
| 35 | —CHR$^{17}$— | H | H | H | H | C$_2$H$_5$ | CH$_3$ | H |
| 36 | —CHR$^{17}$— | H | H | H | H | OCH$_3$ | CH$_3$ | Cl |
| 37 | —CHR$^{17}$— | H | H | H | H | CH$_3$ | CH$_3$ | H |
| 38 | —CHR$^{17}$— | H | H | H | H | F | CH$_3$ | H |
| 39 | —CHR$^{17}$— | H | H | H | H | OCH$_3$ | F | H |
| 40 | —CHR$^{17}$— | H | H | H | H | OCH$_3$ | CH$_3$ | CH$_3$ |
| 41 | —CHR$^{17}$— | H | H | H | H | H | H | H |
| 42 | —CH$_2$CHR$^{17}$— | H | H | H | H | Cl | H | H |
| 43 | —CH$_2$CHR$^{17}$— | H | H | H | H | H | Cl | H |
| 44 | —CH$_2$CHR$^{17}$— | H | H | H | H | H | H | Cl |
| 45 | —CH$_2$CHR$^{17}$— | H | H | H | H | CH$_3$ | H | H |
| 46 | —CH$_2$CHR$^{17}$— | H | H | H | H | H | CH$_3$ | H |
| 47 HCl Salt | —CH$_2$CHR$^{17}$— | H | H | H | H | H | CH$_3$ | H |
| 48 | —CH$_2$CHR$^{17}$— | H | H | H | H | H | H | CH$_3$ |
| 49 | —CH$_2$CHR$^{17}$— | H | H | H | H | OCH$_3$ | Cl | H |
| 50 | —CH$_2$CHR$^{17}$— | H | H | H | H | OCH$_3$ | CH$_3$ | H |
| 51 | —CH$_2$CHR$^{17}$— | H | H | H | H | OCH$_3$ | C$_2$H$_5$ | H |
| 52 | —CH$_2$CHR$^{17}$— | H | H | H | H | OCH$_3$ | CF$_3$ | H |
| 53 | —CH$_2$CHR$^{17}$— | H | H | H | H | OCHF$_2$ | CH$_3$ | H |
| 54 | —CH$_2$CHR$^{17}$— | H | H | H | H | OCF$_3$ | CH$_3$ | H |
| 55 | —CH$_2$CHR$^{17}$— | H | H | H | H | OCH$_3$ | CN | H |
| 56 | —CH$_2$CHR$^{17}$— | H | H | H | H | NH$_2$ | CH$_3$ | H |
| 57 | —CH$_2$CHR$^{17}$— | H | H | H | H | CH=CH$_2$ | CH$_3$ | H |
| 58 | —CH$_2$CHR$^{17}$— | H | H | H | H | CH=CHCH$_3$ | CH$_3$ | H |
| 59 | —CH$_2$CHR$^{17}$— | H | H | H | H | OCH$_3$ | C≡CH | H |
| 60 | —CH$_2$CHR$^{17}$— | H | H | H | H | C≡CCH$_3$ | CH$_3$ | H |
| 61 | —CH$_2$CHR$^{17}$— | CH$_3$ | H | H | H | OCH$_3$ | CH$_3$ | H |
| 62 | —CH$_2$CHR$^{17}$— | H | CH$_3$ | H | H | OCH$_3$ | CH$_3$ | H |
| 63 | —CH$_2$CHR$^{17}$— | H | H | CH$_3$ | H | OCH$_3$ | CH$_3$ | H |
| 64 | —CH$_2$CHR$^{17}$— | H | CH$_3$ | CH$_3$ | H | OCH$_3$ | CH$_3$ | H |
| 65 | —CH$_2$CHR$^{17}$— | H | H | H | H | Cl | H | Cl |
| 66 | —CH$_2$CHR$^{17}$— | H | H | H | H | Cl | Cl | H |
| 67 | —CH$_2$CHR$^{17}$— | H | H | H | H | H | Cl | Cl |
| 68 | —CH$_2$CHR$^{17}$— | H | H | H | H | H | H | H |
| 69 | —CH$_2$CHR$^{17}$— | H | H | H | H | OCH$_3$ | Br | H |
| 70 | —CH$_2$CHR$^{17}$— | H | H | H | Cl | H | H | H |
| 71 | —CH$_2$CHR$^{17}$— | H | H | H | H | OCH$_3$ | CH$_3$ | Cl |
| 72 | —O— | — | H | H | H | H | H | H |
| 73 | —O— | — | H | H | H | OCH$_3$ | Cl | H |
| 74 | —O— | — | H | H | H | H | CH$_3$ | H |
| 75 | —O— | — | H | H | H | OCH$_3$ | CH$_3$ | H |

TABLE 1-continued

Pesticidal Heterocycles

| | | | | | | | | |
|---|---|---|---|---|---|---|---|---|
| 76 | —O— | — | H | H | H | $OCH_3$ | $C_2H_5$ | H |
| 77 | —O— | — | H | H | H | $OCH_3$ | CN | H |
| 78 | —O— | — | H | H | H | $NH_2$ | $CH_3$ | H |
| 79 | —O— | — | H | H | H | $CH=CH_2$ | $CH_3$ | H |
| 80 | —O— | — | H | H | H | $CH=CHCH_3$ | $CH_3$ | H |
| 81 | —O— | — | H | H | H | C≡CH | $CH_3$ | H |
| 82 | —O— | — | H | H | H | C≡$CCH_3$ | $CH_3$ | H |
| 83 | —O— | — | $CH_3$ | H | H | $OCH_3$ | $CH_3$ | H |
| 84 | —O— | — | H | $CH_3$ | H | $OCH_3$ | $CH_3$ | H |
| 85 | —O— | — | $CH_3$ | $CH_3$ | H | $OCH_3$ | $CH_3$ | H |
| 86 | —$OCH_2$— | — | H | H | H | H | H | H |
| 87 | —$OCH_2$— | — | H | H | H | $OCH_3$ | Cl | H |
| 88 | —$OCH_2$— | — | H | H | H | H | $CH_3$ | H |
| 89 | —$OCH_2$— | — | H | H | H | $OCH_3$ | $CH_3$ | H |
| 90 | —$OCH_2$— | — | H | H | H | $OCH_3$ | $C_2H_5$ | H |
| 91 | —$OCH_2$— | — | H | H | H | $OCHF_2$ | $CH_3$ | H |
| 92 | —$OCH_2$— | — | H | H | H | $OCF_3$ | $CH_3$ | H |
| 93 | —$OCH_2$— | — | H | H | H | $NH_2$ | $CH_3$ | H |
| 94 | —$OCH_2$— | — | H | H | H | $CH=CH_2$ | $CH_3$ | H |
| 95 | —$OCH_2$— | — | H | H | H | $CH=CHCH_3$ | $CH_3$ | H |
| 96 | —$OCH_2$— | — | H | H | H | C≡CH | $CH_3$ | H |
| 97 | —$OCH_2$— | — | H | H | H | C≡$CCH_3$ | $CH_3$ | H |
| 98 | —$OCH_2$— | — | $CH_3$ | H | H | $OCH_3$ | $CH_3$ | H |
| 99 | —$OCH_2$— | — | H | $CH_3$ | H | $OCH_3$ | $CH_3$ | H |
| 100 | —$OCH_2$— | — | $CH_3$ | $CH_3$ | H | $OCH_3$ | $CH_3$ | H |
| 101 | —$C_3H_6$— | — | H | H | H | $OCH_3$ | Cl | H |
| 102 | —$C_3H_6$— | — | H | H | H | $OCH_3$ | $CH_3$ | H |
| 103 | —$C_3H_6$— | — | H | H | H | $OCH_3$ | $C_2H_5$ | H |
| 104 | —$C_4H_8$— | — | H | H | H | $OCH_3$ | Cl | H |
| 105 | —$C_4H_8$— | — | H | H | H | $OCH_3$ | $CH_3$ | H |
| 106 | —$C_4H_8$— | — | H | H | H | $OCH_3$ | $C_2H_5$ | H |
| 107 | —$OC_2R_4$— | — | H | H | H | $OCH_3$ | Cl | H |
| 108 | —$OC_2R_4$— | — | H | H | H | $OCH_3$ | $CH_3$ | H |
| 109 | —$OC_2R_4$— | — | H | H | H | $OCH_3$ | $C_2H_5$ | H |
| 110 | —$OC_3H_6$— | — | H | H | H | $OCH_3$ | Cl | H |
| 111 | —$OC_3H_6$— | — | H | H | H | $OCH_3$ | $CH_3$ | H |
| 112 | —$OC_3H_6$— | — | H | H | H | $OCH_3$ | $C_2H_5$ | H |
| 113 | —$CH_2O$— | — | H | H | H | $OCH_3$ | Cl | H |
| 114 | —$CH_2O$— | — | H | H | H | $OCH_3$ | $CH_3$ | H |
| 115 | —$CH_2O$— | — | H | H | H | $OCH_3$ | $C_2H_5$ | H |
| 116 | —$CH_2OCH_2$— | — | H | H | H | $OCH_3$ | Cl | H |
| 117 | —$CH_2OCH_2$— | — | H | H | H | $OCH_3$ | $CH_3$ | H |
| 118 | —$CH_2OCH_2$— | — | H | H | H | $OCH_3$ | $C_2H_5$ | H |
| 119 | —$CH_2OC_2H_4$— | — | H | H | H | $OCH_3$ | Cl | H |
| 120 | —$CH_2OC_2H_4$— | — | H | H | H | $OCH_3$ | $CH_3$ | H |
| 121 | —$CH_2OC_2H_4$— | — | H | H | H | $OCH_3$ | $C_2H_5$ | H |
| 122 | —S— | — | H | H | H | H | H | H |
| 123 | —S— | — | H | H | H | $OCH_3$ | Cl | H |
| 124 | —S— | — | H | H | H | H | $CH_3$ | H |
| 125 | —S— | — | H | H | H | $OCH_3$ | $CH_3$ | H |
| 126 | —S— | — | H | H | H | $OCH_3$ | $C_2H_5$ | H |
| 127 | —S— | — | H | H | H | $CF_3$ | $CH_3$ | H |
| 128 | —S— | — | H | H | H | $OCHF_2$ | $CH_3$ | H |
| 129 | —S— | — | H | H | H | $OCF_3$ | $CH_3$ | H |
| 130 | —S— | — | H | H | H | $NH_2$ | $CH_3$ | H |
| 131 | —S— | — | H | H | H | $CH=CH_2$ | $CH_3$ | H |
| 132 | —S— | — | H | H | H | $CH=CHCH_3$ | $CH_3$ | H |
| 133 | —S— | — | H | H | H | C≡CH | $CH_3$ | H |
| 134 | —S— | — | H | H | H | C≡$CCH_3$ | $CH_3$ | H |
| 135 | —S— | — | $CH_3$ | H | H | $OCH_3$ | $CH_3$ | H |
| 136 | —S— | — | H | $CH_3$ | H | $OCH_3$ | $CH_3$ | H |
| 137 | —S— | — | $CH_3$ | $CH_3$ | H | $OCH_3$ | $CH_3$ | H |
| 138 | —$SCH_2$— | — | H | H | H | $OCH_3$ | Cl | H |
| 139 | —$SCH_2$— | — | H | H | H | $OCH_3$ | $CH_3$ | H |
| 140 | —$SCH_2$— | — | H | H | H | $OCH_3$ | $C_2H_5$ | H |
| 141 | —$SCH_2$— | — | H | H | H | H | $CH_3$ | H |
| 142 | —$CH_2S$— | — | H | H | H | $OCH_3$ | Cl | H |
| 143 | —$CH_2S$— | — | H | H | H | $OCH_3$ | $CH_3$ | H |
| 144 | —$CH_2S$— | — | H | H | H | $OCH_3$ | $C_2H_5$ | H |
| 145 | —$CH_2S(O)$— | — | H | H | H | $OCH_3$ | Cl | H |
| 146 | —$CH_2S(O)$— | — | H | H | H | $OCH_3$ | $CH_3$ | H |
| 147 | —$CH_2S(O)$— | — | H | H | H | $OCH_3$ | $C_2H_5$ | H |
| 148 | —$CH_2S(O)_2$— | — | H | H | H | $OCH_3$ | Cl | H |
| 149 | —$CH_2S(O)_2$— | — | H | H | H | $OCH_3$ | $CH_3$ | H |
| 150 | —$CH_2S(O)_2$— | — | H | H | H | $OCH_3$ | $C_2H_5$ | H |
| 151 | —$N(R^{21})CH_2$— | H | H | H | H | $OCH_3$ | Cl | H |
| 152 | —$N(R^{21})CH_2$— | H | H | H | H | $OCH_3$ | $CH_3$ | H |

TABLE 1-continued

Pesticidal Heterocycles

| 153 | —N(R$^{21}$)CH$_2$— | H | H | H | H | OCH$_3$ | C$_2$H$_5$ | H |
| 154 | —N(R$^{21}$)CH$_2$— | H | H | H | H | OCH$_3$ | n-C$_3$H$_7$ | H |
| 155 | —N(R$^{21}$)CH$_2$— | H | H | H | H | OCH$_3$ | iso-C$_3$H$_7$ | H |
| 156 | —N(R$^{21}$)CH$_2$— | CH | H | H | H | OCH$_3$ | CH$_3$ | H |
| 157 | —CH$_2$N(R$^{21}$)— | H | H | H | H | OCH$_3$ | Cl | H |
| 158 | —CH$_2$N(R$^{21}$)— | H | H | H | H | OCH$_3$ | CH$_3$ | H |
| 159 | —CH$_2$N(R$^{21}$)— | H | H | H | H | OCH$_3$ | C$_2$H$_5$ | H |
| 160 | —CH$_2$N(R$^{21}$)— | H | H | H | H | OCH$_3$ | n-C$_3$H$_7$ | H |
| 161 | —CH$_2$N(R$^{21}$)— | H | H | H | H | OCH$_3$ | iso-C$_6$H$_7$ | H |
| 162 | —CH$_2$N(R$^{21}$)— | CH$_3$ | H | H | H | OCH$_3$ | CH$_3$ | H |

Where
X is —CHR$^{17}$—; and R$^6$, R$^7$, R$^8$, R$^{11}$, R$^{14}$, and R$^{17}$ are hydrogen,
and R$^{12}$ is OCH$_3$:

| Cmpd. No. | R | R$^1$ | R$^{13}$ |
|---|---|---|---|
| 163 | H | CH$_3$ | Cl |
| 164 | H | CH$_3$ | CH$_3$ |
| 165 | H | CH$_3$ | C$_2$H$_3$ |
| 166 | CH$_3$ | CH$_3$ | Cl |
| 167 | CH$_3$ | CH$_3$ | CH$_3$ |
| 168 | CH$_3$ | CH$_3$ | C$_2$H$_5$ |
| 169 | C$_2$H$_5$ | C$_2$H$_5$ | Cl |
| 170 | C$_2$H$_5$ | C$_2$H$_5$ | CH$_3$ |
| 171 | C$_2$H$_5$ | C$_2$H$_5$ | C$_2$H$_5$ |

Where
R, R$^1$, R$^6$, R$^7$, R$^{11}$, R$^{14}$, and R$^{17}$ are hydrogen, and R$^{12}$ is OCH$_3$.

| Cmpd. No. | X | R$^8$ | n | R$^9$ | R$^{10}$ | R$^{13}$ |
|---|---|---|---|---|---|---|
| 172 | —CH$_2$R$^{17}$— | CH$_3$ | — | — | — | Cl |
| 173 | —CH$_2$R$^{17}$— | CH$_3$ | — | — | — | CH$_3$ |
| 174 | —CH$_2$R$^{17}$— | C(O)R$^9$ | — | CH$_3$ | — | Cl |
| 175 | —CH$_2$R$^{17}$— | C(O)R$^9$ | — | CH$_3$ | — | CH$_3$ |
| 176 | —CH$_2$R$^{17}$— | C(O)R$^9$ | — | PhCH$_2$ | — | Cl |
| 177 | —CH$_2$R$^{17}$— | C(O)R$^9$ | — | PhCH$_2$ | — | CH$_3$ |
| 178 | —CH$_2$R$^{17}$— | C(O)OR$^9$ | — | CH$_3$ | — | CH$_3$ |
| 179 | —CH$_2$R$^{17}$— | C(O)OR$^9$ | — | PhCH$_2$ | — | CH$_3$ |
| 180 | —CH$_2$R$^{17}$— | S(O)$_n$R$^9$ | 0 | CH$_3$ | — | CH$_3$ |
| 181 | —CH$_2$R$^{17}$— | S(O)$_n$R$^9$ | 0 | PhCH$_2$ | — | CH$_3$ |
| 182 | —CH$_2$R$^{17}$— | S(O)$_n$R$^9$ | 1 | CH | — | CH$_3$ |
| 183 | —CH$_2$R$^{17}$— | S(O)$_n$R$^9$ | 1 | PhCH$_2$ | — | CH$_3$ |
| 184 | —CH$_2$R$^{17}$— | S(O)$_n$R$^9$ | 2 | CH$_3$ | — | CH$_3$ |
| 185 | —CH$_2$R$^{17}$— | S(O)$_n$R$^9$ | 2 | PhCH$_2$ | — | CH$_3$ |
| 186 | —CH$_2$R$^{17}$— | C(O)N(R$^9$)(R$^{10}$) | — | H | H | CH$_3$ |
| 187 | —CH$_2$R$^{17}$— | C(O)N(R$^9$)(R$^{10}$) | — | H | CH$_3$ | CH$_3$ |
| 188 | —CH$_2$R$^{17}$— | C(O)N(R$^9$)(R$^{10}$) | — | CH$_3$ | CH$_3$ | CH$_3$ |
| 189 | —CH$_2$R$^{17}$— | C(O)N(R$^9$)(R$^{10}$) | — | PHCH$_2$ | H | CH$_3$ |
| 190 | —CH$_2$R$^{17}$— | C(O)N(R$^9$)(R$^{10}$) | — | PhCH$_2$ | CH$_3$ | CH$_3$ |
| 191 | —CH$_2$R$^{17}$— | S(O)$_n$N(R$^9$)(R$^{10}$) | 0 | H | CH$_3$ | CH$_3$ |
| 192 | —CH$_2$R$^{17}$— | S(O)$_n$N(R$^9$)(R$^{10}$) | 0 | CH$_3$ | CH$_3$ | CH$_3$ |
| 193 | —CH$_2$R$^{17}$— | S(O)$_n$N(R$^9$)(R$^{10}$) | 0 | PhCH$_2$ | H | CH$_3$ |
| 194 | —CH$_2$R$^{17}$— | S(O)$_n$N(R$^9$)(R$^{10}$) | 1 | H | CH$_3$ | CH$_3$ |
| 195 | —CH$_2$R$^{17}$— | S(O)$_n$N(R$^9$)(R$^{10}$) | 1 | CH$_3$ | CH$_3$ | CH$_3$ |
| 196 | —CH$_2$R$^{17}$— | S(O)$_n$N(R$^9$)(R$^{10}$) | 1 | PhCH$_2$ | H | CH$_3$ |
| 197 | —CH$_2$R$^{17}$— | S(O)$_n$N(R$^9$)(R$^{10}$) | 2 | H | CH$_3$ | CH$_3$ |
| 198 | —CH$_2$R$^{17}$— | S(O)$_n$N(R$^9$)(R$^{10}$) | 2 | CH$_3$ | CH$_3$ | CH$_3$ |
| 199 | —CH$_2$R$^{17}$— | S(O)$_n$N(R$^9$)(R$^{10}$) | 2 | PhCH$_2$ | H | CH$_3$ |
| 200 | —CH$_2$R$^{17}$— | P(O)(OR$^9$)(OR$^{10}$) | — | C$_2$H$_5$ | C$_2$H$_5$ | CH$_3$ |
| 201 | —CH$_2$CHR$^{17}$— | CN | — | — | — | CH$_3$ |
| 202 | —OCH$_2$— | C(O)R$^9$ | — | CH$_3$ | — | CH$_3$ |
| 203 | —OCH$_2$— | S(O)$_n$N(R$^9$)(R$^{10}$) | 2 | CH$_3$ | CH$_3$ | CH$_3$ |
| 204 | —OCH$_2$— | P(O)(OR$^9$)(OR$^{10}$) | — | CH$_3$ | CH$_3$ | CH$_3$ |
| 205 | —OCH$_2$— | CN | — | — | — | CH$_3$ |
| 206 | —OCH$_2$— | CH$_3$ | — | — | — | CH$_3$ |

TABLE 1-continued

Pesticidal Heterocycles

Where
R and $R^1$ are hydrogen; $R^2$ and $R^3$ taken together is
=NC($R^6$)=C($R^7$)N($R^8$)—; and $R^4$
and $R^5$ taken together is —C($R^{11}$)=C($R^{12}$)C($R^{13}$)C($R^{14}$)—,
where $R^{11}$ and $R^{14}$ are hydrogen:

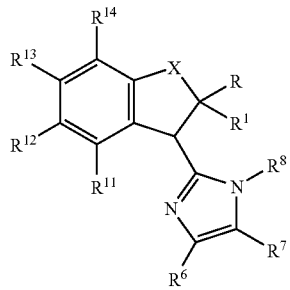

| Cmpd. No. | X | $R^{17}$ | $R^6$ | $R^7$ | $R^8$ | $R^{12}$ | $R^{13}$ |
|---|---|---|---|---|---|---|---|
| 207 | —CHR$^{17}$— | H | H | H | H | OCH$_3$ | Cl |
| 208 | —CHR$^{17}$— | H | H | H | H | OCH$_3$ | CH$_3$ |
| 209 | —CHR$^{17}$— | H | H | H | H | OCH$_3$ | C$_2$H$_5$ |
| 210 | —CHR$^{17}$— | H | CH$_3$ | H | H | OCH$_3$ | CH$_3$ |
| 211 | —CHR$^{17}$— | H | H | CH$_3$ | H | OCH$_3$ | CH$_3$ |
| 212 | —CHR$^{17}$— | H | CH$_3$ | CH$_3$ | CH$_3$ | OCH$_3$ | CH$_3$ |
| 213 | —CHR$^{17}$— | CH$_3$ | H | H | H | OCH$_3$ | CH$_3$ |
| 214 | —CH$_2$CHR$^{17}$— | H | H | H | H | OCH$_3$ | Cl |
| 215 | —CH$_2$CHR$^{17}$— | H | H | H | H | OCH$_3$ | CH$_3$ |
| 216 | —CH$_2$CHR$^{17}$— | H | H | H | H | OCH$_3$ | C$_2$H$_5$ |
| 217 | —CH$_2$CHR$^{17}$— | H | CH$_3$ | H | H | OCH$_3$ | CH$_3$ |
| 218 | —CH$_2$CHR$^{17}$— | H | H | CH$_3$ | H | OCH$_3$ | CH$_3$ |
| 219 | —CH$_2$CHR$^{17}$— | H | CH$_3$ | CH$_3$ | CH$_3$ | OCH$_3$ | CH$_3$ |
| 220 | —CH$_2$CHR$^{17}$— | CH$_3$ | H | H | H | OCH$_3$ | CH$_3$ |
| 221 | —CH$_2$CHR$^{17}$— | H | H | H | PhCH$_2$ | OCH$_3$ | CH$_3$ |
| 222 | —CH$_2$CHR$^{17}$— | H | H | H | C$_2$H$_5$ | OCH$_3$ | CH$_3$ |
| 223 | —CH$_2$CHR$^{17}$— | H | H | H | CH$_3$ | OCH$_3$ | CH$_3$ |
| 224 | —OCH$_2$— | — | H | H | H | OCH$_3$ | Cl |
| 225 | —OCH$_2$— | — | H | H | H | H | CH$_3$ |
| 226 | —OCH$_2$— | — | H | H | H | OCH$_3$ | CH$_3$ |
| 227 | —OCH$_2$— | — | H | H | H | OCH$_3$ | C$_2$H$_5$ |
| 228 | —OCH$_2$— | — | CH$_3$ | H | H | OCH$_3$ | CH$_3$ |
| 229 | —OCH$_2$— | — | H | CH$_3$ | H | OCH$_3$ | CH$_3$ |
| 230 | —OCH$_2$— | — | CH$_3$ | CH$_3$ | CH$_3$ | OCH$_3$ | CH$_3$ |

Where
R, $R^1$, $R^6$, $R^7$, $R^{11}$, $R^{14}$, and $R^{17}$ are hydrogen, and $R^{12}$ is OCH$_3$, and $R^{13}$ is CH$_3$:

| Cmpd. No. | X | $R^8$ | n | $R^9$ | $R^{10}$ |
|---|---|---|---|---|---|
| 231 | —CH$_2$CHR$^{17}$— | CH$_2$OR$^9$ | — | CH$_3$ | — |
| 232 | —CH$_2$CHR$^{17}$— | CH$_2$OC(O)R$^9$ | — | C(CH$_3$)$_3$ | — |
| 233 | —CH$_2$CHR$^{17}$— | S(O)$_n$N(R$^9$)(R$^{10}$) | 2 | CH$_3$ | CH$_3$ |
| 234 | —OCH$_2$— | S(O)$_n$N(R$^9$)(R$^{10}$) | 2 | CH$_3$ | CH$_3$ |

TABLE 1-continued

Pesticidal Heterocycles

Where
R and R¹ are hydrogen; R² and R³ taken together is
=CH(R⁶)=C(R⁷)N(R⁸)—; and R⁴
and R⁵ taken together is —C(R¹¹)=C(R¹²)C(R¹³)=C(R¹⁴)—,
where R¹¹ and R¹⁴ are hydrogen:

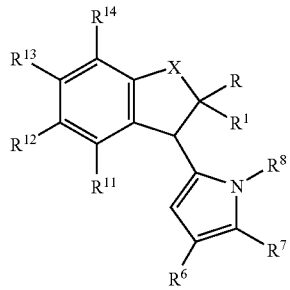

| Cmpd. No. | X | R²¹ | R⁶ | R⁷ | R⁸ | R¹² | R¹³ |
|---|---|---|---|---|---|---|---|
| 235 | —CHR¹⁷— | H | H | H | H | OCH₃ | Cl |
| 236 | —CHR¹⁷— | H | H | H | H | OCH₃ | CH₃ |
| 237 | —CHR¹⁷— | H | H | H | H | OCH₃ | C₂H₅ |
| 238 | —CHR¹⁷— | H | CH₃ | H | H | OCH₃ | CH₃ |
| 239 | —CHR¹⁷— | H | H | CH₃ | H | OCH₃ | CH₃ |
| 240 | —CHR¹⁷— | H | CH₃ | CH₃ | CH₃ | OCH₃ | CH₃ |
| 241 | —CHR¹⁷— | CH₃ | H | H | H | OCH₃ | CH₃ |
| 242 | —CH₂CHR¹⁷— | H | H | H | H | OCH₃ | Cl |
| 243 | —CH₂CHR¹⁷— | H | H | H | H | OCH₃ | CH₃ |
| 244 | —CH₂CHR¹⁷— | H | H | H | H | OCH₃ | C₂H₅ |
| 245 | —CH₂CHR¹⁷— | H | CH₃ | H | H | OCH₃ | CH₃ |
| 246 | —CH₂CHR¹⁷— | H | H | CH₃ | H | OCH₃ | CH₃ |
| 247 | —CH₂CHR¹⁷— | H | CH₃ | CH₃ | CH₃ | OCH₃ | CH₃ |
| 248 | —CH₂CHR¹⁷— | CH₃ | H | H | H | OCH₃ | CH₃ |
| 249 | —OCH₂— | — | H | H | H | OCH₃ | Cl |
| 250 | —OCH₂— | — | H | H | H | H | CH₃ |
| 251 | —OCH₂— | — | H | H | H | OCH₃ | CH₃ |
| 252 | —OCH₂— | — | H | H | H | OCH₃ | C₂H₅ |
| 253 | —OCH₂— | — | CH₃ | H | H | OCH₃ | CH₃ |
| 254 | —OCH₂— | — | H | CH₃ | H | OCH₃ | CH₃ |
| 255 | —OCH₂— | — | CH₃ | CH₃ | CH₃ | OCH₃ | CH₃ |

Where
R and R¹ are hydrogen; R² and R³ taken together is
=CHN=C(R⁷)N(R⁸)— (Tautomer A),
or its tautomer =CHN(R⁸)C(R⁷)=N— (Tautomer B); and R⁴ and R⁵
taken together is —C(R¹¹)=C(R¹²)C(R¹³)=C(R¹⁴)—,
where R¹¹ and R¹⁴ are hydrogen:

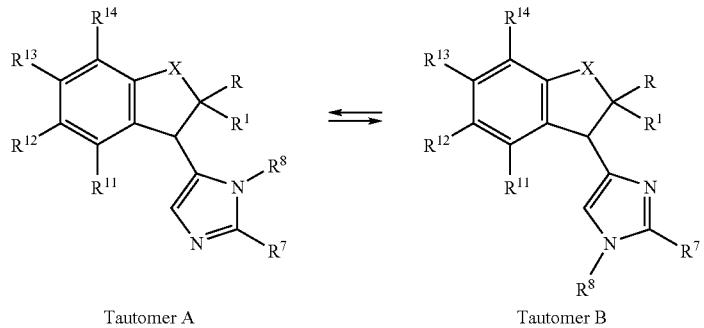

Tautomer A        Tautomer B

| Cmpd. No. | Tautomer | X | R¹⁷ | R⁷ | R⁸ | R¹² | R¹³ |
|---|---|---|---|---|---|---|---|
| 256 | A | —CHR¹⁷— | H | H | H | OCH₃ | Cl |
| 257 | A | —CHR¹⁷— | H | H | H | OCH₃ | CH₃ |
| 258 | A | —CHR¹⁷— | H | H | H | OCH₃ | C₂H₅ |
| 259 | A | —CHR¹⁷— | H | CH₃ | H | OCH₃ | CH₃ |
| 260 | A | —CHR¹⁷— | H | | CH₃ | OCH₃ | CH₃ |

TABLE 1-continued

Pesticidal Heterocycles

| | | | | | | | |
|---|---|---|---|---|---|---|---|
| 261 | A | —CHR$^{17}$— | H | CH$_3$ | CH$_3$ | OCH$_3$ | CH$_3$ |
| 262 | A | —CHR$^{17}$— | CH$_3$ | H | H | OCH$_3$ | CH$_3$ |
| 263 | A | —CH$_2$CHR$^{17}$— | H | H | H | OCH$_3$ | Cl |
| 264 | A | —CH$_2$CHR$^{17}$— | H | H | H | OCH$_3$ | CH$_3$ |
| 265 | A | —CH$_2$CHR$^{17}$— | H | H | H | OCH$_3$ | C$_2$H$_5$ |
| 266 | A | —CH$_2$CHR$^{17}$— | H | CH$_3$ | H | OCH$_3$ | CH$_3$ |
| 267 | A | —CH$_2$CHR$^{17}$— | H | | CH$_3$ | OCH$_3$ | CH$_3$ |
| 268 | A | —CH$_2$CHR$^{17}$— | H | CH$_3$ | CH$_3$ | OCH$_3$ | CH$_3$ |
| 269 | A | —CH$_2$CHR$^{17}$— | CH$_3$ | H | H | OCH$_3$ | CH$_3$ |
| 270 | A | —OCH$_2$— | — | H | H | OCH$_3$ | Cl |
| 271 | A | —OCH$_2$— | — | H | H | H | CH$_3$ |
| 272 | A | —OCH$_2$— | — | H | H | OCH$_3$ | CH$_3$ |
| 273 | A | —OCH$_2$— | — | H | H | OCH$_3$ | C$_2$H$_5$ |
| 274 | A | —OCH$_2$— | — | CH$_3$ | H | OCH$_3$ | CH$_3$ |
| 275 | A | —OCH$_2$— | — | | CH$_3$ | OCH$_3$ | CH$_3$ |
| 276 | A | —OCH$_2$— | — | CH$_3$ | CH$_3$ | OCH$_3$ | CH$_3$ |

| Cmpd. No. | Tautomer | X | R$^7$ | R$^8$ | n | R$^9$ | R$^{10}$ | R$^{12}$ | R$^{13}$ |
|---|---|---|---|---|---|---|---|---|---|
| 277 | B | —OCH$_2$— | H | CN | — | — | — | OCH$_3$ | CH$_3$ |
| 278 | B | —OCH$_2$— | H | S(O)$_n$N(R$^9$)(R$^{10}$) | 2 | CH$_3$ | CH$_3$ | OCH$_3$ | CH$_3$ |

Where
R and R$^1$ are hydrogen; R$^2$ and R$^3$ taken together is
=N(CH$_2$)$_3$N(R$^8$)—; and R$^4$ and
R$^5$ taken together is —C(R$^{11}$)=C(R$^{12}$)C(R$^{13}$)=C(R$^{14}$)—,
where R$^{11}$ and R$^{14}$ are hydrogen:

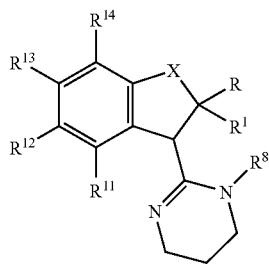

| Cmpd. No. | X | R$^{17}$ | R$^8$ | R$^{12}$ | R$^{13}$ |
|---|---|---|---|---|---|
| 279 | —CHR$^{17}$— | H | H | OCH$_3$ | Cl |
| 280 | —CHR$^{17}$— | H | H | OCH$_3$ | CH$_3$ |
| 281 | —CHR$^{17}$— | H | H | OCH$_3$ | C$_2$H$_5$ |
| 282 | —CHR$^{17}$— | H | CH$_3$ | OCH$_3$ | CH$_3$ |
| 283 | —CHR$^{17}$— | CH$_3$ | H | OCH$_3$ | CH$_3$ |
| 284 | —CHR$^{17}$— | CH$_3$ | CH$_3$ | OCH$_3$ | CH$_3$ |
| 285 | —CH$_2$CHR$^{17}$— | H | H | OCH$_3$ | Cl |
| 286 | —CH$_2$CHR$^{17}$— | H | H | OCH$_3$ | CH$_3$ |
| 287 | —CH$_2$CHR$^{17}$— | H | H | OCH$_3$ | C$_2$H$_5$ |
| 288 | —CH$_2$CHR$^{17}$— | H | CH$_3$ | OCH$_3$ | CH$_3$ |
| 289 | —CH$_2$CHR$^{17}$— | CH$_3$ | H | OCH$_3$ | CH$_3$ |
| 290 | —CH$_2$CHR$^{17}$— | CH$_3$ | CH$_3$ | OCH$_3$ | CH$_3$ |
| 291 | —OCH$_2$— | — | H | OCH$_3$ | Cl |
| 292 | —OCH$_2$— | — | H | H | CH$_3$ |
| 293 | —OCH$_2$— | — | H | OCH$_3$ | CH$_3$ |
| 294 | —OCH$_2$— | — | H | OCH$_3$ | C$_2$H$_5$ |
| 295 | —OCH$_2$— | — | CH$_3$ | OCH$_3$ | CH$_3$ |

TABLE 1-continued

Pesticidal Heterocycles

Where
R and $R^1$ are hydrogen; $R^2$ and $R^3$ taken together is
=NCH($R^6$)CH($R^7$)S—; and $R^4$
and $R^5$ taken together is —C($R^{11}$)=C($R^{12}$)C($R^{13}$)=C($R^{14}$)—,
where $R^{11}$ and $R^{14}$ are hydrogen:

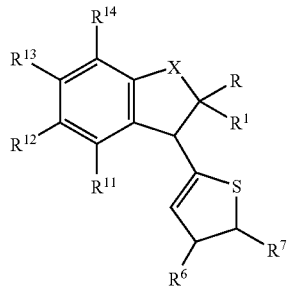

| Cmpd. No. | X | $R^{17}$ | $R^6$ | $R^7$ | $R^{12}$ | $R^{13}$ |
|---|---|---|---|---|---|---|
| 296 | —CHR$^{17}$— | H | H | H | OCH$_3$ | Cl |
| 297 | —CHR$^{17}$— | H | H | H | OCH$_3$ | CH$_3$ |
| 298 | —CHR$^{17}$— | H | H | H | OCH$_3$ | C$_2$H$_5$ |
| 299 | —CHR$^{17}$— | H | CH$_3$ | H | OCH$_3$ | CH$_3$ |
| 300 | —CHR$^{17}$— | H | H | CH$_3$ | OCH$_3$ | CH$_3$ |
| 301 | —CHR$^{17}$— | H | CH$_3$ | CH$_3$ | OCH$_3$ | CH$_3$ |
| 302 | —CHR$^{17}$— | CH$_3$ | H | H | OCH$_3$ | CH$_3$ |
| 303 | —CH$_2$CHR$^{17}$— | H | H | H | OCH$_3$ | Cl |
| 304 | —CH$_2$CHR$^{17}$— | H | H | H | OCH$_3$ | CH$_3$ |
| 305 | —CH$_2$CHR$^{17}$— | H | H | H | OCH$_3$ | C$_2$H$_5$ |
| 306 | —CH$_2$CHR$^{17}$— | H | CH$_3$ | H | OCH$_3$ | CH$_3$ |
| 307 | —CH$_2$CHR$^{17}$— | H | H | CH$_3$ | OCH$_3$ | CH$_3$ |
| 308 | —CH$_2$CHR$^{17}$— | H | CH$_3$ | CH$_3$ | OCH$_3$ | CH$_3$ |
| 309 | —CH$_2$CHR$^{17}$— | CH$_3$ | H | H | OCH$_2$ | CH$_3$ |
| 310 | —OCH$_2$— | — | H | H | OCH$_3$ | Cl |
| 311 | —OCH$_2$— | — | H | H | H | CH$_3$ |
| 312 | —OCH$_2$— | — | H | H | OCH$_3$ | CH$_3$ |
| 313 | —OCH$_2$— | — | H | H | OCH$_3$ | C$_2$H$_5$ |
| 314 | —OCH$_2$— | — | CH$_3$ | H | OCH$_3$ | CH$_3$ |
| 315 | —OCH$_2$— | — | H | CH$_3$ | OCH$_3$ | CH$_3$ |
| 316 | —OCH$_2$— | — | CH$_3$ | CH$_3$ | OCH$_3$ | CH$_3$ |

Where
R and $R^1$ are hydrogen; $R^2$ and $R^3$ taken together is
=NCH($R^6$)CH($R^7$)O—; and $R^4$
and $R^5$ taken together is —C($R^{11}$)=C($R^{12}$)C($R^{13}$)=C($R^{14}$)—,
where $R^{11}$ and $R^{14}$ are hydrogen:

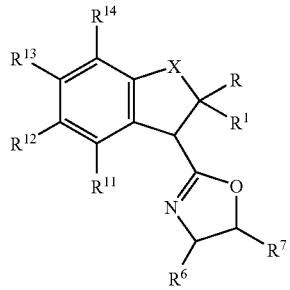

| Cmpd. No. | X | $R^{17}$ | $R^6$ | $R^7$ | $R^{12}$ | $R^{13}$ |
|---|---|---|---|---|---|---|
| 317 | —CHR$^{17}$— | H | H | H | OCH$_3$ | Cl |
| 318 | —CHR$^{17}$— | H | H | H | OCH$_3$ | CH$_3$ |
| 319 | —CHR$^{17}$— | H | H | H | OCH$_3$ | C$_2$H$_5$ |
| 320 | —CHR$^{17}$— | H | CH$_3$ | H | OCH$_3$ | CH$_3$ |
| 321 | —CHR$^{17}$— | H | H | CH$_3$ | OCH$_3$ | CH$_3$ |
| 322 | —CHR$^{17}$— | H | CH$_3$ | CH$_3$ | OCH$_3$ | CH$_3$ |
| 323 | —CHR$^{17}$— | CH$_3$ | H | H | OCH$_3$ | CH$_3$ |
| 324 | —CH$_2$CHR$^{17}$— | H | H | H | OCH$_3$ | Cl |

TABLE 1-continued

Pesticidal Heterocycles

| | | | | | | |
|---|---|---|---|---|---|---|
| 325 | —CH$_2$CHR$^{17}$— | H | H | H | OCH$_3$ | CH$_3$ |
| 326 | —CH$_2$CHR$^{17}$— | H | H | H | OCH$_3$ | C$_2$H$_5$ |
| 327 | —CH$_2$CHR$^{17}$— | H | CH$_3$ | H | OCH$_3$ | CH$_3$ |
| 328 | —CH$_2$CHR$^{17}$— | H | H | CH$_3$ | OCH$_3$ | CH$_3$ |
| 329 | —CH$_2$CHR$^{17}$— | H | CH$_3$ | CH$_3$ | OCH$_3$ | CH$_3$ |
| 330 | —CH$_2$CHR$^{17}$— | CH$_3$ | H | H | OCH$_3$ | CH$_3$ |
| 331 | —OCH$_2$— | — | H | H | OCH$_3$ | Cl |
| 332 | —OCH$_2$— | — | H | H | H | CH$_3$ |
| 333 | —OCH$_2$— | — | H | H | OCH$_3$ | CH$_3$ |
| 334 | —OCH$_2$— | — | H | H | OCH$_3$ | C$_2$H$_5$ |
| 335 | —OCH$_2$— | — | CH$_3$ | H | OCH$_3$ | CH$_3$ |
| 336 | —OCH$_2$— | — | H | CH$_3$ | OCH$_3$ | CH$_3$ |
| 337 | —OCH$_2$— | — | CH$_3$ | CH$_3$ | OCH$_3$ | CH$_3$ |

Where
R and R$^1$ are hydrogen; R$^2$ and R$^3$ taken together is
=NCH(R$^6$)CH(R$^7$)N(R$^8$)—; and
R$^4$ and R$^5$ taken together is —SC(R$^{15}$)=C(R$^{16}$)—:

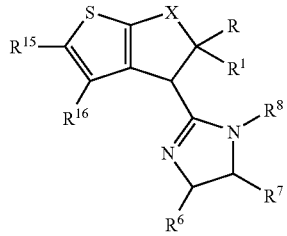

| Cmpd. No. | X | R$^{17}$ | R$^6$ | R$^7$ | R$^8$ | R$^{15}$ | R$^{16}$ |
|---|---|---|---|---|---|---|---|
| 338 | —CHR$^{17}$— | H | H | H | H | H | H |
| 339 | —CHR$^{17}$— | H | H | CH$_3$ | H | Cl | Cl |
| 340 | —CHR$^{17}$— | H | CH$_3$ | H | H | CH$_3$ | OCH$_3$ |
| 341 | —CHR$^{17}$— | H | H | CH$_3$ | H | C$_2$H$_5$ | Cl |
| 342 | —CHR$^{17}$— | H | CH$_3$ | CH$_3$ | H | OCH$_3$ | CH$_3$ |
| 343 | —CHR$^{17}$— | H | CH$_3$ | CH$_3$ | CH$_3$ | OCH$_3$ | CH$_3$ |
| 344 | —CHR$^{17}$— | CH$_3$ | H | H | H | OCH$_3$ | CH$_3$ |
| 345 | —CH$_2$CHR$^{17}$— | H | H | H | H | H | H |
| 346 | —CH$_2$CHR$^{17}$— | H | H | CH$_3$ | H | Cl | Cl |
| 347 | —CH$_2$CHR$^{17}$— | H | CH$_3$ | H | H | CH$_3$ | OCH$_3$ |
| 348 | —CH$_2$CHR$^{17}$— | H | H | CH$_3$ | H | C$_2$H$_5$ | Cl |
| 349 | —CH$_2$CHR$^{17}$— | H | CH$_3$ | CH$_3$ | H | OCH$_3$ | CH$_3$ |
| 350 | —CH$_2$CHR$^{17}$— | H | CH$_3$ | CH$_3$ | CH$_3$ | OCH$_3$ | CH$_3$ |
| 351 | —CH$_2$CHR$^{17}$— | CH$_3$ | H | H | H | OCH$_3$ | CH$_3$ |
| 352 | —OCH$_2$— | — | H | H | H | H | H |
| 353 | —OCH$_2$— | — | H | CH$_3$ | H | Cl | Cl |
| 354 | —OCH$_2$— | — | CH$_3$ | H | H | CH$_3$ | OCH$_3$ |
| 355 | —OCH$_2$— | — | CH$_3$ | CH$_3$ | H | C$_2$H$_5$ | Cl |
| 356 | —OCH$_2$— | — | CH$_3$ | CH$_3$ | CH$_3$ | OCH$_3$ | CH$_3$ |

Where
R and R$^1$ are hydrogen; R$^2$ and R$^3$ taken together is
=NCH(R$^6$)CH(R$^7$)N(R$^8$)—; and
R$^4$ and R$^5$ taken together is —C(R$^{15}$)=C(R$^{16}$)S—:

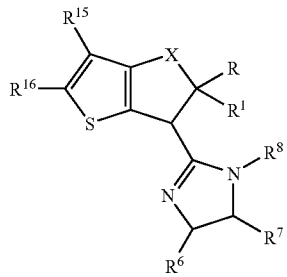

| Cmpd. No. | X | R$^{17}$ | R$^6$ | R$^7$ | R$^8$ | R$^{15}$ | R$^{16}$ |
|---|---|---|---|---|---|---|---|
| 357 | —CHR$^{17}$— | H | H | H | H | H | H |
| 358 | —CHR$^{17}$— | H | H | H | H | Cl | Cl |
| 359 | —CHR$^{17}$— | H | H | H | H | CH$_3$ | OCH$_3$ |

TABLE 1-continued

Pesticidal Heterocycles

| | | | | | | | |
|---|---|---|---|---|---|---|---|
| 360 | —CHR$^{17}$— | H | H | H | H | C$_2$H$_5$ | Cl |
| 361 | —CHR$^{17}$— | H | H | H | H | OCH$_3$ | CH$_3$ |
| 362 | —CHR$^{17}$— | H | CH$_3$ | H | H | OCH$_3$ | CH$_3$ |
| 363 | —CHR$^{17}$— | H | H | CH$_3$ | H | OCH$_3$ | CH$_3$ |
| 364 | —CHR$^{17}$— | H | CH$_3$ | CH$_3$ | H | OCH$_3$ | CH$_3$ |
| 365 | —CHR$^{17}$— | H | CH$_3$ | CH$_3$ | CH$_3$ | OCH$_3$ | CH$_3$ |
| 366 | —CHR$^{17}$— | CH$_3$ | H | H | H | OCH$_3$ | CH$_3$ |
| 367 | —CH$_2$CHR$^{17}$— | H | H | H | H | H | H |
| 368 | —CH$_2$CHR$^{17}$— | H | H | H | H | Cl | Cl |
| 369 | —CH$_2$CHR$^{17}$— | H | H | H | H | CH$_3$ | OCH$_3$ |
| 370 | —CH$_2$CHR$^{17}$— | H | H | H | H | C$_2$H$_5$ | Cl |
| 371 | —CH$_2$CHR$^{17}$— | H | H | H | H | OCH$_3$ | CH$_3$ |
| 372 | —CH$_2$CHR$^{17}$— | H | CH$_3$ | H | H | OCH$_3$ | CH$_3$ |
| 373 | —CH$_2$CHR$^{17}$— | H | H | CH$_3$ | H | OCH$_3$ | CH$_3$ |
| 374 | —CH$_2$CHR$^{17}$— | H | CH$_3$ | CH$_3$ | H | OCH$_3$ | CH$_3$ |
| 375 | —CH$_2$CHR$^{17}$— | H | CH$_3$ | CH$_3$ | CH$_3$ | OCH$_3$ | CH$_3$ |
| 376 | —CH$_2$CHR$^{17}$— | CH$_3$ | H | H | H | OCH$_3$ | CH$_3$ |
| 377 | —OCH$_2$— | — | H | H | H | H | H |
| 378 | —OCH$_2$— | — | H | H | H | Cl | Cl |
| 379 | —OCH$_2$— | — | H | H | H | CH$_3$ | OCH$_3$ |
| 380 | —OCH$_2$— | — | H | H | H | C$_2$H$_5$ | Cl |
| 381 | —OCH$_2$— | — | H | H | H | OCH$_3$ | CH$_3$ |
| 382 | —OCH$_2$— | — | CH$_3$ | H | H | OCH$_3$ | CH$_3$ |
| 383 | —OCH$_2$— | — | H | CH$_3$ | H | OCH$_3$ | CH$_3$ |
| 384 | —OCH$_2$— | — | CH$_3$ | CH$_3$ | H | OCH$_3$ | CH$_3$ |
| 385 | —OCH$_2$— | — | CH$_3$ | CH$_3$ | CH$_3$ | OCH$_3$ | CH$_3$ |

Where
R and R$^1$ are hydrogen; R$^2$ and R$^3$ taken together is
=NCH(R$^6$)CH(R$^7$)N(R$^8$)—; and
R$^4$ and R$^5$ taken together is —CH=C(R$^{15}$)N=CH—:

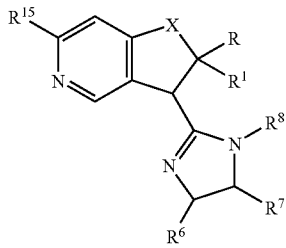

| Cmpd. No. | X | R$^{17}$ | R$^6$ | R$^7$ | R$^8$ | R$^{15}$ |
|---|---|---|---|---|---|---|
| 386 | —CHR$^{17}$— | H | H | H | H | H |
| 387 | —CHR$^{17}$— | H | H | H | H | Cl |
| 388 | —CHR$^{17}$— | H | H | H | H | CH$_3$ |
| 389 | —CHR$^{17}$— | H | H | H | H | C$_2$H$_5$ |
| 390 | —CHR$^{17}$— | H | H | H | H | OCH$_3$ |
| 391 | —CHR$^{17}$— | H | CH$_3$ | H | H | OCH$_3$ |
| 392 | —CHR$^{17}$— | H | H | CH$_3$ | H | OCH$_3$ |
| 393 | —CHR$^{17}$— | H | CH$_3$ | CH$_3$ | H | OCH$_3$ |
| 394 | —CHR$^{17}$— | H | CH$_3$ | CH$_3$ | CH$_3$ | OCH$_3$ |
| 395 | —CHR$^{17}$— | CH$_3$ | H | H | H | OCH$_3$ |
| 396 | —CH$_2$CHR$^{17}$— | H | H | H | H | H |
| 397 | —CH$_2$CHR$^{17}$— | H | H | H | H | Cl |
| 398 | —CH$_2$CHR$^{17}$— | H | H | H | H | CH$_3$ |
| 399 | —CH$_2$CHR$^{17}$— | H | H | H | H | C$_2$H$_5$ |
| 400 | —CH$_2$CHR$^{17}$— | H | H | H | H | OCH$_3$ |
| 401 | —CH$_2$CHR$^{17}$— | H | CH$_3$ | H | H | OCH$_3$ |
| 402 | —CH$_2$CHR$^{17}$— | H | H | CH$_3$ | H | OCH$_3$ |
| 403 | —CH$_2$CHR$^{17}$— | H | CH$_3$ | CH$_3$ | H | OCH$_3$ |
| 404 | —CH$_2$CHR$^{17}$— | H | CH$_3$ | CH$_3$ | CH$_3$ | OCH$_3$ |
| 405 | —CH$_2$CHR$^{17}$— | CH$_3$ | H | H | H | OCH$_3$ |
| 406 | —OCH$_2$— | — | H | H | H | H |
| 407 | —OCH$_2$— | — | H | H | H | Cl |
| 408 | —OCH$_2$— | — | H | H | H | CH$_3$ |
| 409 | —OCH$_2$— | — | H | H | H | C$_2$H$_5$ |
| 410 | —OCH$_2$— | — | H | H | H | OCH$_3$ |
| 411 | —OCH$_2$— | — | CH$_3$ | H | H | OCH$_3$ |
| 412 | —OCH$_2$— | — | H | CH$_3$ | H | OCH$_3$ |
| 413 | —OCH$_2$— | — | CH$_3$ | CH$_3$ | H | OCH$_3$ |
| 414 | —OCH$_2$— | — | CH$_3$ | CH$_3$ | CH$_3$ | OCH$_3$ |

TABLE 1-continued

Pesticidal Heterocycles

Where
R and $R^1$ are hydrogen; $R^2$ and $R^3$ taken together is
—OCH($R^6$)CH($R^7$)N($R^8$)N=;
and $R^4$ and $R^5$ taken together is —C($R^{11}$)=C($R^{12}$)C($R^{13}$)=C($R^{14}$)—,
where $R^6$, $R^7$, $R^{11}$ and $R^{14}$ are hydrogen, $R^{12}$ is $OCH_3$,
and $R^{13}$ is $CH_3$:

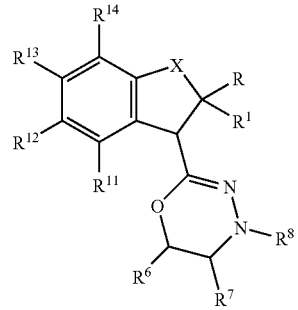

| Cmpd. No. | X | $R^{17}$ | $R^8$ | n | $R^9$ | $R^{10}$ |
|---|---|---|---|---|---|---|
| 415 | —CH$_2$CHR$^{17}$— | H | H | — | — | — |
| 416 | —CH$_2$CHR$^{17}$— | H | C(O)R$^9$ | — | NH$_2$ | — |
| 417 | —CH$_2$CHR$^{17}$— | H | CN | — | — | — |
| 418 | —CH$_2$CHR$^{17}$— | H | S(O)$_n$N(R$^9$)(R$^{10}$) | 2 | CH$_3$ | CH$_3$ |
| 419 | —CH$_2$CHR$^{17}$— | H | P(O)(OR$^9$)(OR$^{10}$) | — | CH$_3$ | CH$_3$ |
| 420 | —CH$_2$CHR$^{17}$— | H | P(O)(NR$^9$R$^{10}$)(NR$^9$R$^{10}$) | — | CH$_3$ | CH$_3$ |
| 421 | —CH$_2$CHR$^{17}$— | H | CHO | — | — | — |
| 422 | —OCH$_2$— | — | H | — | — | — |
| 423 | —OCH$_2$— | — | C(O)R$^9$ | — | NH$_2$ | — |
| 424 | —OCH$_2$— | — | CN | — | — | — |
| 425 | —OCH$_2$— | — | S(O)$_n$N(R$^9$)(R$^{10}$) | 2 | CH$_3$ | CH$_3$ |
| 426 | —OCH$_2$— | — | P(O)(OR$^9$)(OR$^{10}$) | — | CH$_3$ | CH$_3$ |
| 427 | —OCH$_2$— | — | P(O)(NR$^9$R$^{10}$)(NR$^9$R$^{10}$) | — | CH$_3$ | CH$_3$ |
| 428 | —OCH$_2$— | — | CHO | — | — | — |

Where
$R^2$ and $R^3$ taken together is =NCH($R^6$)CH($R^7$)N($R^8$)—;
and $R^4$ and $R^5$ taken together is —C($R^{11}$)=C($R^{12}$)C($R^{13}$)=C($R^{14}$),
where R, $R^1$, $R^6$, $R^7$, $R^{11}$, $R^{14}$, and $R^{17}$ are
hydrogen; $R^{12}$ is $OCH_3$, and $R^{13}$ is $CH_3$:

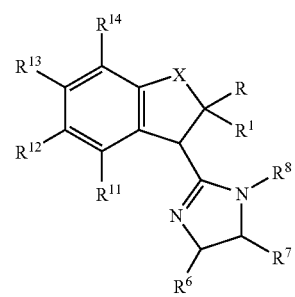

| Cmpd. No. | X | $R^8$ | n | $R^9$ |
|---|---|---|---|---|
| 429 | —CH$_2$R$^{17}$— | NH$_2$ | — | — |
| 430 | —CH$_2$R$^{17}$— | CH$_2$R$^9$ | — | Ph |
| 431 | —CH$_2$R$^{17}$— | S(O)$_n$R$^9$ | I | CH$_3$ |
| 432 | —CH$_2$R$^{17}$— | Si(R$^9$)$_3$ | — | CH$_3$ |
| 433 | —CH$_2$R$^{17}$— | CH=N(R$^9$) | — | CH$_3$ |
| 434 | —CH$_2$CHR$^{17}$— | NH$_2$ | — | — |
| 435 | —CH$_2$CHR$^{17}$— | CH$_2$R$^9$ | — | Ph |
| 436 | —CH$_2$CHR$^{17}$— | Si(R$^9$)$_3$ | — | CH$_3$ |
| 437 | —CH$_2$CHR$^{17}$— | CH=N(R$^9$) | — | CH$_3$ |
| 438 | —OCH$_2$— | NH$_2$ | — | — |
| 439 | —OCH$_2$— | CH$_2$R$_9$ | — | Ph |
| 440 | —OCH$_2$— | Si(R$^9$)$_3$ | — | CH$_3$ |
| 441 | —OCH$_2$— | CH=N(R$^9$) | — | CH$_3$ |

TABLE 1-continued

Pesticidal Heterocycles

| Cmpd. No. | X | $R^8$ | Y | $R^a$ |
|---|---|---|---|---|
| 442 | —$CH_2R^{17}$— | Y | N-oxide | — |
| 443 | —$CH_2R^{17}$— | $OR^a$ | — | H |
| 444 | —$CH_2R^{17}$— | $OR^a$ | — | $CH_3$ |
| 445 | —$CH_2CHR^{17}$— | Y | N-oxide | — |
| 446 | —$CH_2CHR^{17}$— | $OR^a$ | — | H |
| 447 | —$CH_2CHR^{17}$— | $OR^a$ | — | $CH_3$ |
| 448 | —$OCH_2$— | Y | N-oxide | — |
| 449 | —$OCH_2$— | $OR^a$ | — | H |
| 450 | —$OCH_2$— | $OR^a$ | — | $CH_3$ |

TABLE 2

Pesticidal Heterocycles Characterizing Data

| Cmpd. No. | Emperical Formulae | Physical State |
|---|---|---|
| 1 | $C_{13}H_{16}N_2$ | Solid |
| 2 | $C_{13}H_{16}N_2$ HCl | Solid |
| 3 | $C_{13}H_{15}FN_2$ | Solid |
| 4 | $C_{13}H_{15}ClN_2O$ | Solid |
| 5 | $C_{13}H_{15}IN_2O$ | Solid |
| 6 | $C_{14}H_{18}N_2O$ | Solid |
| 7 | $C_{14}H_{18}N_2O$ HCl | Solid |
| 8 | $C_{12}H_{13}ClN_2$ | Solid |
| 9 | $C_{12}H_{13}ClN_2$ | Solid; mp 122-130° C. |
| 10 | $C_{12}H_{14}ClN_2$ HCl | Solid; mp 250-254° C. |
| 11 | $C_{12}H_{12}Cl_2N_2$ | Solid |
| 12 | $C_{13}H_{16}N_2$ HCl | Solid |
| 13 | $C_{13}H_{16}N_2$ HCl | Solid |
| 14 | $C_{13}H_{16}N_2$ | Solid |
| 15 | $C_{13}H_{16}N_2$ HCl | Solid |
| 16 | $C_{14}H_{18}N_2$ HCl | Solid |
| 17 | $C_{12}H_{13}FN_2$ HCl | Solid |
| 18 | $C_{12}H_{14}N_2O$ HBr | Solid |
| 19 | $C_{13}H_{15}ClN_2O$ | Solid |
| 22 | $C_{12}H_{12}Cl_2N_2$ | Solid |
| 23 | $C_{13}H_{15}ClN_2$ | Solid |
| 24 | $C_{14}H_{16}F_2N_2O$ | Solid |
| 26 | $C_{13}H_{17}N_3$ | Solid |
| 27 | $C_{15}H_{17}N_2$ | Solid |
| 29 | $C_{15}H_{16}N_2$ | Solid |
| 31 | $C_{15}H_{20}N_2O$ | Solid |
| 35 | $C_{15}H_{20}N_2$ | Solid |
| 36 | $C_{14}H_{17}ClN_2O$ | Solid |
| 37 | $C_{14}H_{18}N_2$ | Solid |
| 38 | $C_{13}H_{15}FN_2$ | Solid |
| 39 | $C_{13}H_{15}FN_2O$ | Solid |
| 40 | $C_{15}H_{20}N_2O$ | Solid |
| 42 | $C_{13}H_{15}ClN_2$ HCl | Solid |
| 43 | $C_{13}H_{15}ClN_2$ | Solid |
| 44 | $C_{13}H_{16}ClN_2$ HCl | Solid; mp 195-199° C. |
| 45 | $C_{14}H_{19}N_2$ HCl | Solid |
| 46 | $C_{14}H_{18}N_2$ | Solid |
| 47 | $C_{14}H_{18}N_2$ HCl | — |
| 48 | $C_{14}H_{18}N_2$ | Solid |
| 50 | $C_{15}H_{20}N_2O$ | Solid |
| 51 | $C_{16}H_{22}N_2O$ | Solid |
| 52 | $C_{15}H_{17}F_3N_2O$ | Solid |
| 55 | $C_{15}H_{17}N_3O$ | Solid |
| 59 | $C_{16}H_{18}N_2O$ | Oil |
| 65 | $C_{13}H_{14}Cl_2N_2$ | Solid |
| 66 | $C_{13}H_{14}Cl_2N_2$ | Solid |
| 67 | $C_{13}H_{14}Cl_2N_2$ | Liquid |
| 68 | $C_{13}H_{16}N_2$ | Solid |
| 69 | $C_{14}H_{17}BrN_2O$ | Solid |
| 70 | $C_{13}H_{15}ClN_2$ | Solid |
| 71 | $C_{15}H_{19}ClN_2O$ | Solid |
| 88 | $C_{13}H_{16}N_2O$ | Solid |
| 89 | $C_{14}H_{18}N_2O_2$ | Solid |
| 139 | $C_{14}H_{18}N_2OS$ | Solid |
| 141 | $C_{13}H_{16}N_2S$ | Solid |
| 152 | $C_{14}H_{19}N_3O$ | Solid |
| 201 | $C_{16}H_{19}N_3O$ | Oil |
| 202 | $C_{16}H_{20}N_2O_3$ | Solid |
| 203 | $C_{16}H_{23}N_2O_4S$ | Oil |
| 204 | $C_{16}H_{23}N_2O_5P$ | Oil |
| 205 | $C_{15}H_{17}N_3O_2$ | Solid |
| 206 | $C_{15}H_{20}N_2O_2$ | Oil |
| 215 | $C_{15}H_{18}N_2O$ | Solid, 197-229° C. |
| 221 | $C_{22}H_{24}N_2O$ | Oil |
| 222 | $C_{17}H_{22}N_2O$ | Oil |
| 223 | $C_{16}H_{20}N_2O$ | Oil |
| 226 | $C_{14}H_{16}N_2O_2$ | Solid |
| 231 | $C_{17}H_{22}N_2O_2$ | Oil |
| 232 | $C_{21}H_{28}N_2O_3$ | Oil |
| 233 | $C_{17}H_{23}N_3O_3S$ | Oil |
| 234 | $C_{16}H_{21}N_3O_4S$ | Oil |
| 257 | $C_{14}H_{16}N_2O$ | Solid mp 68-70° C. |
| 264 | $C_{15}H_{18}N_2O$ | Solid |
| 272 | $C_{14}H_{16}N_2O_2$ | Solid |
| 278 | $C_{16}H_{21}N_3O_4S$ | Solid, mp 138-139° |

One method for assessing the insecticidal activity of a compound, for example, a compound of formula I of the present invention, can be a comparison of the changes in insect populations during a period of time in treated and untreated loci that initially have known insect populations. For example, cotton aphid may vacate a treated host plant in a state of hyperactivity caused by coming in contact with a test compound. Once the cotton aphid has left the treated host plant, it most likely will die from lack of nutrients that it normally would gather by feeding on the host plant. Accordingly, the compounds of the present invention were tested for insecticidal activity by observing any decrease in population of cotton aphid (*Aphis gossypii*) on treated cotton plants from aphid hyperactivity caused by a test compound, when compared to like populations of cotton aphid on untreated plants. These tests were conducted in the following manner:

For each rate of application of test compound, two seven- to-ten days old cotton seedlings (*Gossypium hirsutium*) grown in 7.6 cm diameter pots were selected for the test. Each test plant was infested with about 120 adult cotton aphids by placing onto each test plant cuttings of leaves from cotton plants grown in a cotton aphid colony. Once infested, the test plants were maintained for up to about 12 hours to allow complete translocation of the aphids onto the test plant. A solution comprising 300 part per million (ppm) of each test compound was prepared by dissolving 3 milligrams of the test compound in 1 mL of acetone. Each solution was then diluted with 9 mL of a solution of 0.03 mL of polyoxyethylene(10) isooctylphenyl ether in 100 mL of water. About 2.5 mL of solution of each test compound was needed to spray each replicate of test plant (5 mL total for each test compound). If needed, the solution of 300 ppm of test compound was serially diluted with a solution of 10% acetone and 300 ppm of polyoxyethylene(10) isooctylphenyl ether in water to provide solutions of each test compound for lower rates of application, for example, 100 ppm, 10 ppm, or 3 ppm. Each replicate of test plant was sprayed with the solutions of test compound until run-off on both the upper and lower surfaces of the leaves. All the test plants were sprayed using a DeVilbus Atomizer Model 152 (Sunrise Medical, Carlsbad, Calif.) at a pressure of about 0.63-0.74 kilogram per square centimeter from a distance of about 30.5 centimeters from the test plants. For comparison purposes, a solution of a standard, such as amitraz or demethylchlordimeform (DCDM), prepared in a manner analogous to that set forth above, as well as a solution of 10% acetone and 300 ppm of polyoxyethylene(10) isooctylphenyl ether in water containing no test compound were also sprayed onto test plants. Upon completion of spraying the solutions of test compound, the solution of standard, and the solution containing no test compound, the plants were allowed to dry. Upon completion of drying, the test plants were placed in a tray containing about 2.5 centimeters of water, where they were maintained in a growth chamber for at least 24 hours. After this time, each plant was assessed for decreased aphid population from aphid hyperactivity caused by the test compound when compared to the population of aphids on test plants not treated with test compound. A test compound was designated as possessing insecticidal activity (SA) if there was at least a 50% reduction in cotton aphid population on plants sprayed with that compound. If at least 75% of the cotton aphid population had left the test plant, a test compound was designated as being more insecticidally active (A). If few or no cotton aphids had left the plant, the test compound was termed as inactive (I).

Insecticidal activity data at selected rates of application are provided in Table 3. The test compounds of formula I are identified by numbers that correspond to those in Table 1.

TABLE 3

Pesticidal Heterocycles
Insecticidal Activity in Tests Against Cotton Aphid

| Cmpd. No. | Repellency of Cotton Aphid SA | A |
|---|---|---|
| 1 |   | X |
| 2 | X |   |
| 3 | X |   |
| 4 |   | X |
| 5 | X |   |
| 6 |   | X |
| 7 |   | X |
| 8 |   | X |
| 9 |   | X |
| 10 | X |   |
| 11 | X |   |
| 12 |   | X |
| 13 | X |   |
| 14 | X |   |
| 15 | X |   |
| 16 |   | X |
| 17 |   | X |
| 18 |   | X |
| 19 |   | X |
| 22 |   | X |
| 23 | X |   |
| 24[1] | X |   |
| 26[1] | X |   |
| 27 |   | X |
| 29 | X |   |
| 31[1] |   | X |
| 35 | X |   |
| 36[1] |   | X |
| 37 |   | X |
| 38 |   | X |
| 39[3] |   | X |
| 40 |   | X |
| 42 | X |   |
| 43 |   | X |
| 44 |   | X |
| 45 |   | X |
| 46 |   | X |
| 47 |   | X |
| 48 |   | X |
| 50 |   | X |
| 51[1] |   | X |
| 52[1] |   | X |
| 55[2] |   | X |
| 59[1] | X |   |
| 65[1] |   | X |
| 66[1] |   | X |
| 67[1] |   | X |
| 68 |   | X |
| 69[1] |   | X |
| 70[1] | X |   |
| 71[1] |   | X |
| 88 |   | X |
| 89[1] |   | X |
| 139 |   | X |
| 141 |   | X |
| 152[1] | X |   |
| 201[1] |   | X |
| 202[1] |   | X |
| 203[2] |   | X |
| 204[2] |   | X |
| 205[1] |   | X |
| 206[1] | X |   |
| 215[2] |   | X |
| 221[1] |   | X |
| 222[1] | X |   |
| 223[2] |   | X |
| 226 |   | X |
| 231[1] |   | X |
| 232[1] |   | X |
| 233[1] |   | X |
| 234[1] |   | X |
| 257 |   | X |
| 264[1] |   | X |
| 272[1] |   | X |
| 278[2] |   | X |

Unless noted otherwise, insects exposed to plants for 24 hours (24 hour exposure period) that were treated at an application rate of 300 ppm of test compound.
[1] Insects exposed to treated plants for 48 hours (48 hour exposure period).
[2] Insects exposed to treated plants for 72 hours (72 hour exposure period).
[3] Insects exposed to plants for 72 hours (72 hour exposure period) that were treated at an application rate of 1000 ppm of test compound.

As set forth in the foregoing table, the majority of the compounds of formula I in Table 3 caused at least a 75% reduction (A) in population of cotton aphid, while the remaining compounds of formula I in Table 3 caused at least a 50% reduction (SA) in cotton aphid population.

While this invention has been described with an emphasis upon preferred embodiments, it will be understood by those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed:

1. An insecticidal composition comprising at least one of an insecticidally effective amount of a compound of formula I and at least one insecticidally compatible carrier therefor, wherein the compound of formula I is:

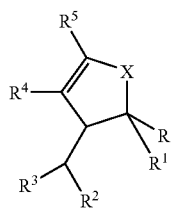

I wherein
- R and $R^1$ are independently selected from hydrogen and alkyl;
- $R^2$ and $R^3$ are taken together to form a five- or six-membered ring selected from =NC($R^6$)=C($R^7$)N($R^8$)—, =CHC($R^6$)=C($R^7$)N($R^8$)—, =CHN=C($R^7$)N($R^8$)—, =N(CH$_2$)$_3$N($R^8$)—, =NCH($R^6$)CH($R^7$)S—, =NCH($R^6$)CH($R^7$)O—, =CHCH=CHCH=N—, =NN=CHN($R^8$)—, =NN=NN($R^8$)—, —OCH($R^6$)CH($R^7$)N($R^8$)N=, and tautomers thereof;

where
$R^6$ and $R^7$ are independently selected from hydrogen and alkyl;
$R^8$ is selected from hydrogen, alkyl, amino, nitro, cyano, formyl, —CH$_2$$R^9$, —CH$_2$OR$^9$, —C(O)R$^9$, —C(O)OR$^9$, —CH$_2$OC(O)R$^9$, —C(O)N(R$^9$)(R$^{10}$), —S(O)$_n$R$^9$—, —S(O)$_n$N(R$^9$)(R$^{10}$) where n is 0, 1, or 2, —Si(R$^9$)$_3$, —CH=N(R$^9$), —P(O)(OR$^9$)(OR$^{10}$), —P(O)(NR$^9$R$^{10}$)(NR$^9$R$^{10}$), and Y, wherein Y represents i) an N-oxide of said five- or six-membered ring, or ii) forms an OR$^a$ linkage wherein R$^a$ is selected from hydrogen and alkyl; and,
$R^9$ and $R^{10}$ are independently selected from hydrogen, alkyl, alkylcarbonyl, alkoxycarbonyl aryl, arylalkyl, and heteroaryl, wherein aryl is optionally substituted with one or more substituent independently selected from halogen, alkyl, or haloalkyl;
—$R^4$ and $R^5$ taken together are —C(R$^{11}$)=C(R$^{12}$)C(R$^{13}$)=C(R$^{14}$)—, where
$R^{11}$ and $R^{14}$ are independently selected from hydrogen, halogen, and methyl;
$R^{12}$ is selected from hydrogen, halogen, amino, (C$_1$-C$_2$)alkyl, methoxy, halomethoxy, (C$_2$-C$_3$)alkenyl, and (C$_2$-C$_3$)alkynyl; and
$R^{13}$ is selected from hydrogen, halogen, cyano, (C$_1$-C$_2$)alkyl, hydroxyl, methoxy, halomethyl, and (C$_2$-C$_3$)alkynyl;
—X is selected from —O—, —OCH$_2$—, —S—, and —SCH$_2$—; and
agriculturally-acceptable salts thereof.

2. An insecticidal composition of claim 1, wherein $R^2$ and $R^3$ taken together is =NC(R$^6$)=C(R$^7$)N(R$^8$)—, or =CHN=C(R$^7$)N(R$^8$)—, and tautomers thereof, where $R^8$ is selected from hydrogen, cyano, —S(O)$_n$N(R$^9$)(R$^{10}$), and —P(O)(OR$^9$)(OR$^{10}$), where n is 2, and $R^9$ and $R^{10}$ are independently selected from hydrogen and alkyl; $R^4$ and $R^5$ are taken together to form a fused ring, where $R^4$ and $R^5$ together is —C(R$^{11}$)=C(R$^{12}$)C(R$^{13}$)=C(R$^{14}$), where $R^{11}$ is hydrogen, $R^{12}$ is selected from halogen and methoxy, and $R^{13}$ is selected from halogen and (C$_1$-C$_2$)alkyl; and, X is selected, —OCH$_2$—, and —SCH$_2$—.

3. An insecticidal composition of claim 2, wherein $R^9$ and $R^{10}$ are each methyl; $R^{12}$ is selected from chlorine and methoxy; $R^{13}$ is selected from chlorine and methyl; and, $R^{14}$ is selected from hydrogen, chlorine and methyl; and X is OCH$_2$—.

4. An insecticidal composition of claim 3, wherein $R^2$ and $R^3$ taken together is =NC(R$^6$)=C(R$^7$)N(R$^8$)—.

5. An insecticidal composition of claim 3, wherein $R^2$ and $R^3$ taken together is =CHN=C(R$^7$)N(R$^8$)—.

6. An insecticidal composition of claim 1, further comprising one or more second compounds.

7. An insecticidal composition of claim 2, further comprising one or more second compounds.

8. An insecticidal composition of claim 3, further comprising one or more second compounds.

9. An insecticidal composition of claim 4, further comprising one or more second compounds.

10. An insecticidal composition of claim 5, further comprising one or more second compounds.

* * * * *